(12) United States Patent
Sharpe et al.

(10) Patent No.: US 10,481,069 B2
(45) Date of Patent: Nov. 19, 2019

(54) METHOD AND APPARATUS FOR MONITORING AND OPTIMIZING MICROFLUIDIC PARTICLE SORTING

(75) Inventors: Johnathan Charles Sharpe, Hamilton (NZ); Donald F. Perrault, Jr., Brighton, MA (US); Blair Morad, Belmont, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 194 days.

(21) Appl. No.: 13/342,756

(22) Filed: Jan. 3, 2012

(65) Prior Publication Data

US 2012/0277902 A1 Nov. 1, 2012

Related U.S. Application Data

(60) Provisional application No. 61/429,339, filed on Jan. 3, 2011.

(51) Int. Cl.
*B07C 5/34* (2006.01)
*G01N 15/14* (2006.01)
(Continued)

(52) U.S. Cl.
CPC ....... *G01N 15/1404* (2013.01); *B07C 5/3425* (2013.01); *G01N 15/1484* (2013.01);
(Continued)

(58) Field of Classification Search
CPC .......... G01N 15/1404; G01N 15/1485; G01N 2015/149; G05B 13/00; G05B 13/24; B07C 5/3425; B07C 5/361
(Continued)

(56) References Cited

U.S. PATENT DOCUMENTS 4,756,427 A 7/1988 Gohde et al.
5,257,206 A * 10/1993 Hanson ......................... 700/273
(Continued)

FOREIGN PATENT DOCUMENTS

FR 2888932 A1 1/2007
WO 2003/089157 A1 10/2003
(Continued)

OTHER PUBLICATIONS

English Translation of WO 2007009983 (A1); Jan. 25, 2007; Haguet et al.*
(Continued)

*Primary Examiner* — Joseph C Rodriguez
(74) *Attorney, Agent, or Firm* — McCarter & English, LLP; David R. Burns

(57) ABSTRACT

Particle processing systems and methods utilize a sort monitoring system to monitor an operational characteristic for a particle sorting system. The operational characteristic may be related to the performance and operation of a sorter or a group of sorters in the particle sorting system. The operational characteristic may be monitored based on monitoring particles for an output of a sorter or of a group of sorters. Operational characteristics which may be monitored include sort error, sort fraction, yield, purity and recovery percentage. The sort monitoring system may evaluate the monitored operational characteristic, for example, as related to sort performance, and take an action, for example, a corrective action or a notifying action, based on the evaluation of the operational characteristic.

42 Claims, 18 Drawing Sheets

(51) Int. Cl.
*B07C 5/342* (2006.01)
*G01N 15/10* (2006.01)

(52) U.S. Cl.
CPC .............. *G01N 2015/1081* (2013.01); *G01N 2015/149* (2013.01)

(58) Field of Classification Search
USPC ................ 209/552; 422/502, 503, 105, 110; 700/28, 32, 219, 223
See application file for complete search history.

(56) References Cited

U.S. PATENT DOCUMENTS

| | | | |
|---|---|---|---|
| 5,837,200 A | 11/1998 | Diessel et al. | |
| 5,998,212 A * | 12/1999 | Corio | G01N 15/1427 209/3.1 |
| 6,351,676 B1 * | 2/2002 | Thomas | 700/28 |
| 6,372,506 B1 * | 4/2002 | Norton | G01N 15/1404 209/127.4 |
| 6,475,364 B1 * | 11/2002 | Dubrow et al. | 204/455 |
| 6,616,823 B2 * | 9/2003 | Kopf-Sill | 204/602 |
| 7,157,274 B2 * | 1/2007 | Bohm et al. | 435/325 |
| 7,214,298 B2 * | 5/2007 | Spence | B01L 3/502761 204/450 |
| 8,140,300 B2 * | 3/2012 | Dunne et al. | 702/186 |
| 8,392,135 B2 * | 3/2013 | McClain et al. | 702/81 |
| 8,660,340 B2 * | 2/2014 | Shibuya et al. | 382/159 |
| 8,705,031 B2 * | 4/2014 | Sedoglavich | G01N 15/1404 356/337 |
| 8,709,817 B2 * | 4/2014 | Durack et al. | 436/63 |
| 8,709,825 B2 * | 4/2014 | Durack et al. | 436/180 |
| 8,727,131 B2 * | 5/2014 | Desphande | B07C 5/02 209/552 |
| 8,765,062 B2 * | 7/2014 | Linder et al. | 422/82.05 |
| 8,889,072 B2 * | 11/2014 | Degeal | B07C 5/342 422/67 |
| 8,975,595 B2 * | 3/2015 | Norton | G01N 15/14 250/428 |
| 9,074,978 B2 * | 7/2015 | Lo | G01P 5/001 |
| 9,134,221 B2 * | 9/2015 | Lo | G01N 15/1459 |
| 9,696,257 B2 * | 7/2017 | Fox | G01N 21/64 |
| 2003/0000835 A1 * | 1/2003 | Witt et al. | 204/451 |
| 2003/0234210 A1 | 12/2003 | Deshpande et al. | |
| 2004/0086159 A1 * | 5/2004 | Lary et al. | 382/128 |
| 2005/0112541 A1 * | 5/2005 | Durack | C12N 5/0612 435/2 |
| 2005/0178700 A1 | 8/2005 | Tyvoll et al. | |
| 2005/0211556 A1 | 9/2005 | Childers et al. | |
| 2007/0117086 A1 * | 5/2007 | Evans et al. | 435/4 |
| 2011/0001963 A1 * | 1/2011 | Durack | G01N 15/1434 356/301 |
| 2012/0078531 A1 * | 3/2012 | Lo | G01N 15/1459 702/21 |
| 2014/0034555 A1 * | 2/2014 | Foster et al. | 209/233 |
| 2014/0097129 A1 * | 4/2014 | Foster | B01L 3/502761 209/579 |
| 2014/0170697 A1 * | 6/2014 | Sharpe et al. | 435/30 |
| 2014/0216128 A1 * | 8/2014 | Trotter et al. | 73/19.01 |
| 2014/0220620 A1 * | 8/2014 | Durack et al. | 435/34 |
| 2014/0309782 A1 * | 10/2014 | Sharpe et al. | 700/266 |
| 2015/0050688 A1 * | 2/2015 | Thrasher et al. | 435/34 |
| 2015/0093817 A1 * | 4/2015 | Foster et al. | 435/288.7 |
| 2015/0192511 A1 * | 7/2015 | Wagner | C12N 5/0612 435/287.2 |

FOREIGN PATENT DOCUMENTS

| | | | | |
|---|---|---|---|---|
| WO | WO 2005/022147 A1 | 3/2005 | | |
| WO | WO 2007009983 A1 * | 1/2007 | ........ | B01L 3/502753 |
| WO | WO 2010/104993 A2 | 9/2010 | | |
| WO | WO 2014/031900 A1 * | 2/2014 | ............. | G01N 15/14 |

OTHER PUBLICATIONS

Invitation to Pay Additional Fees issued in International Application No. PCT/US2012/020089, dated May 2, 2012.
International Preliminary Report on Patentability issued in International Application No. PCT/US2012/020089, dated Aug. 8, 2013.
International Search Report and Written Opinion issued in International Application No. PCT/US2012/020089, dated Jul. 8, 2013.
European Office Action for Application No. 12702628.4, dated Sep. 4, 2018. 5 pages.

* cited by examiner

METHOD AND APPARATUS FOR MONITORING AND OPTIMIZING MICROFLUIDIC PARTICLE SORTING

CROSS-REFERENCE TO RELATED APPLICATIONS

The present application claims priority to U.S. Provisional Patent Application No. 61/429,399, filed Jan. 3, 2011 (entitled "Method and Apparatus for Monitoring and Optimizing Particle Sorting"), which is incorporated herein by reference in its entirety.

TECHNICAL FIELD

The present disclosure relates to particular particle processing systems and methods. More particularly, the present disclosure relates to systems and methods for monitoring operational characteristics of a particle sorting system.

BACKGROUND

In the fields of biology and medicine, there is often a need for high throughput analysis and sorting of particles. One well known technique for sorting particles is droplet deflection. See, for example, U.S. Pat. No. 6,372,506. In droplet deflection a stream of suspended particles is broken into individual droplets, for example, using a piezoelectric mechanism. At the point of droplet formation, an electrical charging element is used to selectively charge each droplet. The charged droplet then free falls through an electrostatic field which deflects the charged particle into one of a plurality of receiving containers.

Another technique for deflecting particles involves utilizing switching or pressure mechanisms to divert a volume of fluid containing a particle into a selected branch channel of a flow-path defined on a microfluidic chip. See, for example, U.S. Pat. No. 6,808,075, which is hereby incorporated, herein, in its entirety.

SUMMARY

Systems and methods are disclosed which utilize a sort monitoring system to monitor an operational characteristic (such as particle count, sort error, sort fraction, yield, purity, recovery, enrichment, or the like) of a particle sorting system, specifically a flow sorter system. The operational characteristic may generally relate to an operation of a sorter or a group of sorters in the particle processing system. The sort monitoring system may include a sensor system for monitoring a particle or particles from an output of a sorter or a group of sorters, for example, for detecting the presence or absence of a particle or particles from an output of a sorter or a group of sorters. The sensor system may also be configured to monitor one or more particle characteristics. In exemplary embodiments, the sort monitoring system may include a plurality of sensor systems, for example, for monitoring particles at different locations, or for monitoring different particle characteristics at a same location.

In exemplary embodiments, the sort monitoring system may monitor a particle count for an output of a sorter or a group of sorters, which may be used, for example, to calculate yield or evaluate the accuracy of a sort. For example, a monitored particle count may be compared to an expected particle count. In this way, the sort monitoring system may be used to monitor sorting errors, for example contamination of an output.

In some embodiments, the sort monitoring system may identify individual particles outputted from a sorter or a group of sorters. For example, a particle outputted from a sorter or group of sorters may be classified for verification purposes relative to a sort criteria or protocol. In exemplary embodiments, the sort monitoring system may track the path of an individual particle, for example, using a plurality of sensor systems at different locations.

In exemplary embodiments, an operational characteristic may relate to an operational mode such as purification (maximizing purity of a sorted sample), recovery (maximizing retention of a particle type in a sorted sample), enrichment (minimizing a particle type in a sorted sample), or the like for a sorter or group of sorters. For example, the sort monitoring system may monitor purity (percentage of selected particle type(s) in a monitored sample), recovery percentage (percentage of selected particle type(s) recovered from an initial sample), enrichment percentage (percentage of selected particle type(s) removed from an initial sample), or the like.

In exemplary embodiments, the sort monitoring system may evaluate the operational characteristic and take an action, based on a result of the evaluation of the operational characteristic of the particle sorting system. Actions may include notification actions, for example, communicating sort-related information to a user or a computer program. Actions may also include corrective or proactive actions, for example, adjusting an operation of a sorter or group of sorters in order to correct, maintain or improve performance.

In exemplary embodiments, the sort monitoring system may include a notification system for communicating to a user or to a computer program particle status (such as the presence or absence of a particle or particles) sort status, sort errors, risk of a sort errors, sort statistics, or other sort-related information. In exemplary embodiments, the notification system may notify a user or compute program about a status of operations, for example a change in operations, for a sorter or a group of sorters. The sort monitoring system may also include a control system for adjusting operations of a particle sorting system. For example, the control system may adjust sample flow, fluid flow, sample alignment, inter-particle spacing, sort rate, or the like, for a sorter or group of sorters. In some embodiments, the control system may adjust operations so as to optimize one or more operational characteristics and do so with minimal user intervention. For example, the control system may maximize a sort rate while maintaining a level of sort accuracy. In exemplary embodiments, the control system may optimize multiple-channel sorting, for example, by selectively activating and/or halting particular flow-channels in a multiple-channel particle sorting system.

DESCRIPTION OF EXEMPLARY EMBODIMENT(S)

Figure 1:
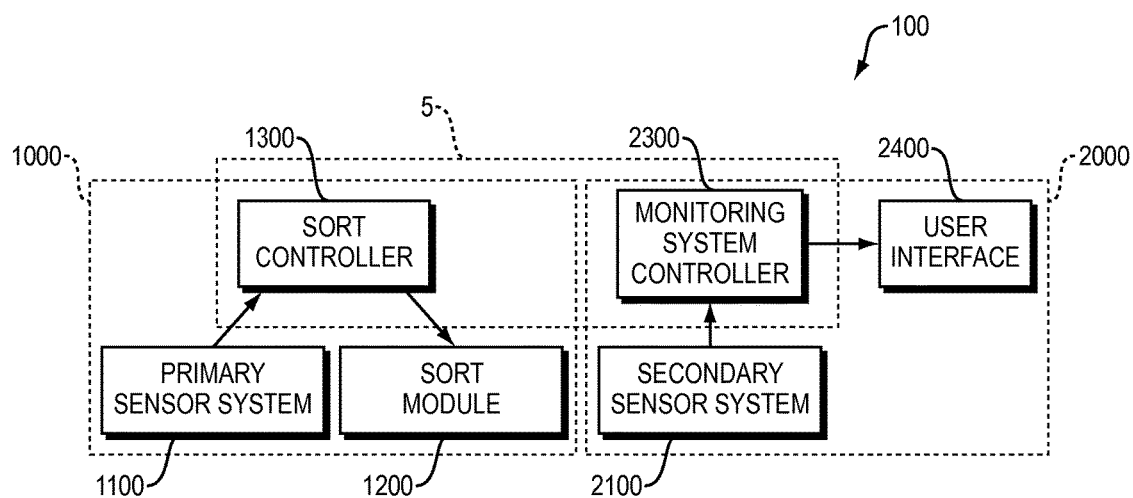
FIG. 1 depicts an exemplary particle processing system, according to the present disclosure, the particle processing system including a particle sorting system and a sort monitoring system.

Particle processing systems and methods are disclosed herein which utilize a sort monitoring system to monitor an operational characteristic for a particle sorting system, for example a microfluidic particle sorting system. The operational characteristic for the particle sorting system is a characteristic related to the performance and operation of the particle sorting system. More particularly, the operational characteristic may be related to the performance and operation of a sorter or a group of sorters in the particle sorting system. In some embodiments, the operational characteristic may be monitored based on monitoring an output of a sorter or a group of sorters in the particle sorting system and, more particularly, may be monitored based on detecting particles or an absence of particles from an output of a sorter or a group of sorters.

Examples of operational characteristics which may be monitored according to the systems and methods of the present disclosure include but are not limited to particle count, particle type, sort error, sort fraction, yield, purity, recovery percentage, enrichment percentage, or the like. The sort monitoring system may further be configured to evaluate the monitored operational characteristic, for example, as related to sort performance, and, in some embodiments, take an action, for example, a notification action or a corrective or proactive action, based on the evaluation of the operational characteristic.

The sort modules and sorting systems of the present disclosure may be characterized as flow sorters and may generally be structurally and functionally distinguished from drop sorters, as discussed herein. The sort modules and sorting systems of the present disclosure preferably utilize microfluidics and comprise a closed-channel system for sorting particles. Microfluidic particle sorting technology takes advantages of a closed, sterile, and scalable approach to efficiently and/or quickly sort large numbers of particles. To this end, a plurality of sort modules may be combined, for example, on a single microfluidic chip substrate. Sensing and sorting functionalities may further interface with the chip or be included thereon.

The terms flow-channel and flow-path as used herein refer to a pathway formed in or through a medium that allows for movement of fluids, such as liquids and gases. Typical flow-channels in a microfluidic system have cross-sectional dimensions between about 1.0 µm and about 500 µm. In some embodiments, flow-channels have cross-sectional dimensions between about 25 µm and about 250 µm. In further embodiments, flow-channels have cross-sectional dimensions between about 50 µm and about 200 µm. One of ordinary skill in the art will be able to determine appropriate channel dimensions, for example, cross-sectional dimension, length, volume, or the like, of a flow-channel. A flow-channel can have any selected shape or arrangement.

Examples of possible flow-channel cross-sectional geometries may include but are not limited to a linear or non-linear configuration, a U-shaped configuration, a V-shaped configuration, a D-shaped configuration, a C-shaped configuration, a circular configuration, or the like.

The term "particle" refers to a discrete unit of matter. For example, particles may include atoms, ions, molecules, cells, agglomerates, or the like. Particles may also refer to (macro) molecular species such as proteins, enzymes, polynucleotides, or the like. Particles are typically between 1 nm and 10 mm in diameter. In some embodiments, particles are between 100 nm and 200 µm in diameter. In further embodiments, particles are between 1 µm and 15 µm in diameter. Particles may be naturally occurring or synthetic, or may combine natural and synthetic components within a single particle. Particles may refer to biological particles. For example, particles may include cells (for example, blood platelets, white blood cells, tumorous cells or embryonic cells, spermatozoa, to name a few), liposomes, proteoliposomes, yeast, bacteria, viruses, pollens algae, or the like. Particles may also refer to non-biological particles. For example, particles may include metals, minerals, polymeric substances, glasses, ceramics, composites, or the like.

The term "sensor," as used herein, refers to a device for measuring one or more characteristics of an object, such as a particle.

The terms "upstream" and "downstream" are referenced relative to a directional flow of particles in a flow-path and not particular elements or features within an apparatus.

With initial reference to FIG. 1, an exemplary particle processing system 100 is depicted. The particle processing system 100 includes a particle sorting system 1000 and a sort monitoring system 2000.

The particle sorting system 1000 generally provides for particle sorting, for example, according to the detect-decide-deflect principle ((i) detection of one or more predetermined characteristics of a particle such as optical absorption, light scatter, extinction, polarization, fluorescent intensity, size, shape, charge, magnetic field, or the like; (ii) evaluation of the particle based on the detected characteristic(s); and (iii) sorting of the particle based on the evaluation thereof). The particle sorting system 1000 may typically include a primary sensor system 1100 (also referred to as a sort sensor system) for detecting one or more predetermined characteristics of a particle. The particle sorting system 1000 may also typically contain a sort module 1200, including a sorter, for sorting a particle, for example, based at least in part on the one or more predetermined particle characteristics detected by the primary sensor system 1100. In some embodiments, the primary sensor system 1100 may be operatively coupled directly or indirectly to the sort module 1200. In other embodiments, the primary sensor system 1100 may be included in the sort module 1200.

In exemplary embodiments, the particle sorting system 1000 may include a plurality of primary sensor systems and/or a plurality of sort modules. For example, the particle sorting system 1000 may include a plurality of primary sensor systems, each included in or operatively coupled directly or indirectly to a sort module. In some embodiments, the plurality of primary sensor systems may be included in or operatively coupled directly or indirectly to a same sort module, for example, for detection of different particle characteristics. In other embodiments, the plurality of primary sensor systems may be included in or operatively coupled directly or indirectly to different sort modules. It is also noted that in some embodiments a primary sensor system may be included in or operatively coupled directly or indirectly to a plurality of sort modules, for example, to make optimal use of space in the particle sorting system 1000.

In exemplary embodiments, the particle sorting system 1000 may include or be operatively associated directly or indirectly with a sort controller 1300, for example, for controlling the primary sensor system 1100 and the sorter of the sort module 1200. One of ordinary skill in the art will be able to appreciate that sort controller 1300 may be implemented in whole or in part via programming associated with a programmable processor, for example, processor 5.

The sort monitoring system 2000 is configured to monitor and, in some embodiments, evaluate and possibly take an action based on the evaluation of an operational characteristic of the particle sorting system 1000. The sort monitoring system 2000 may include a secondary sensor system 2100 (also referred to as a monitor sensor system) for monitoring particles downstream of the sorter of the sort module 1200. The sort monitoring system 2000 may monitor an operational characteristic of the particle sorting system 1000, based on the secondary sensor system 2100, for example, based on the secondary sensor system 2100 detecting a presence of a particle or an absence of a particle downstream of the sorter.

In exemplary embodiments, the sort monitoring system 2000 may include or be operatively associated directly or indirectly with a monitoring system controller 2300. The monitoring system controller 2300 may be responsive to the secondary sensor system 2100. In exemplary embodiments, the monitoring system controller 2300 may be configured to evaluate an operational characteristic or a set of operational characteristics of the particle sorting system 1000 and take an action, based on a result of the evaluation. For example, the monitoring system controller 2300 may be configured to notify a user about and/or adjust, optimize, maintain or track the performance of an operation of the particle sorting system 1000 based on the evaluation of the operational characteristic or the set of operational characteristics, for example, if a sort error is detected. As with the sorting system controller 1300, the monitoring system controller 2300 may be implemented in whole or in part via programming associated with a programmable processor, for example, the same processor 5 as sort controller 1300 or a different programmable processor. The monitoring system controller 2300 may further include or be associated with a user interface 2400.

Figure 2:
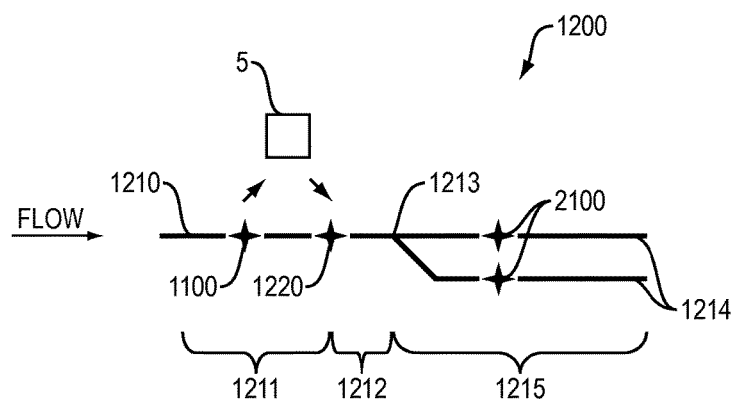
FIG. 2 depicts an exemplary sort module for use in a particle sorting system, according to the present disclosure, wherein the sort the flow-path of the sort module includes two output branch channels.

With reference to FIG. 2 an exemplary embodiment of a sort module 1200 for a particle sorting system, for example, the particle sorting system 1000 of FIG. 1, is depicted. The sort module 1200 includes a branched channel flow-path 1210. In exemplary embodiments, the flow-path 1210 may be a flow-channel, for example, a microchannel, defined in a substrate, for example, of a microfluidic chip. The sort module 1200 may be configured to receive a stream of particles suspended in a carrier fluid, through the flow-path 1210 in a flow direction. The flow-path 1210 may include a primary sensing region 1211, a sort region 1212 in proximity to the primary sensing region 1211 and a branch point 1213 downstream of the sort region 1212 where the flow-path 1210 branches into a plurality of output branch channels 1214. A secondary detection region 1215 may be included extending downstream of the sort region 1212, for example downstream of the branch point 1213 along the output branch channels 1214 of the flow-path 1210.

The sort module 1200 may include or be operatively associated with a primary sensor system 1100 for detecting particles at the primary sensing region 1211. The primary sensor system 1100 may detect one or more predetermined particle characteristics which may serve as sorting criteria for the sort module 1200. In some embodiments, the primary sensor system 1100 may detect particle velocity, for example, for controlling sort timing on a particle-by-particle basis. Sort module 1200 may include or be operatively associated with a programmable processor 5 for controlling the primary sensor system 1100. In exemplary embodiments, the sort module 1200 may include or be operatively associated with a plurality of primary sensor systems, for example, for detecting different particle characteristics.

Figure 3:
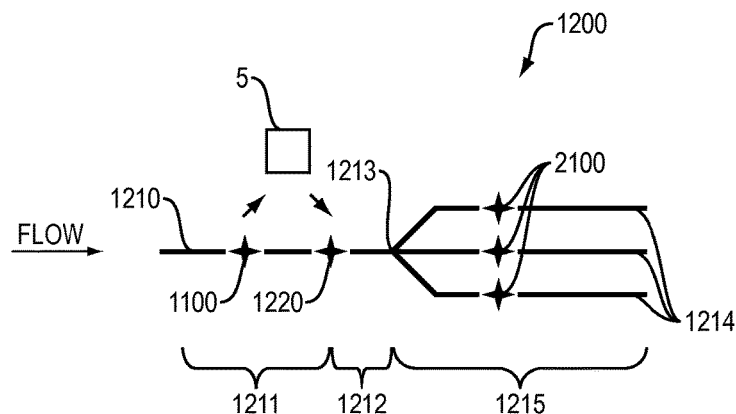
FIG. 3 depicts an exemplary sort module for use in a particle sorting system, according to the present disclosure, wherein the sort the flow-path of the sort module includes three output branch channels.

The sort module 1200 may include a sorter 1220 for selectively sorting particles at the sort region 1212. For example, the sorter 1220 may selectively sort a particle by deflecting it into one of the output branch channels 1214 of the flow-path 1210. It is noted that while the sort module 1200 depicted in FIG. 2 includes two output branch channels 1214 for flow-path 210, the present disclosure is not limited to such an embodiment. Indeed, in some embodiments (such as depicted in FIG. 3) the flow-path 1210 of the sort module 1200 may include more than two output branch channels 1214. In exemplary embodiments, the sorter 1220 may be configured such that deflected particles sort into one of one or more "active" branch channels of the flow-path 1210 and non-deflected particles sort into one of one or more "passive" branch channels of the flow-path 1210.

In some embodiments, the sorter 1220 may be responsive to an actuator which may be included in or operatively coupled directly or indirectly to the sort module 1200. In exemplary embodiments, the actuator may be a mechanical, optical, acoustic, magnetic, optomechanical, electromagnetic or other mechanism for deflecting or otherwise facilitating/enabling the sorting of a particle. The sort module 1200 may include or be operatively associated with a programmable processor for controlling the sorter 1220, for example, the same processor 5 as for the primary sensor system 1100 or a different programmable processor.

The sort module 1200 may be associated with a sort monitoring system as described herein, for example, the sort monitoring system 2000 of FIG. 1. Thus, the sort module 1200 may be associated with secondary sensor systems 2100 for monitoring particles at the secondary detection region 1215. Thus, for example, each of the secondary sensor systems 2100 may detect a presence of a particle or an absence of a particle, for one of the output branch channels 1214. In exemplary embodiments, a plurality of secondary sensor systems may be used for monitoring particles for a same one of the output branch channels 1214, for example, for detecting different particle characteristics. In some embodiments, the secondary sensors may be configured to monitor particles flowing from one of the output branch channels 1214, for example, in a capillary tube connected to the output branch channel.

With reference to FIG. 3 another exemplary embodiment of a sort module 1200 for a particle sorting system is depicted. The sort module 1200 includes a branched flow-path 1210 including a primary sensing region 1211 for association with a primary sensor system 1100 a sort region 1212 in proximity to the primary sensing region 1211 and a branch point 1213 downstream of the sort region 1212 where the flow-path 1210 branches into a plurality of output branch channels 1214. As depicted in FIG. 3, the flow-path 1210 advantageously branched into three output branch channels 1214. The sort module 1200 may include a sorter 1220 for selectively sorting particles at the sort region 1212. For example, the sorter 1220 may selectively sort a particle by deflecting it into one of the output branch channels 1214 of the flow-path 1210. A secondary detection region 1215 for association with secondary sensor systems 2100 of a sort monitoring system may be included extending downstream of the sort region 1212. In particular, secondary sensor systems 2100 may be used to monitor particles at the secondary detection region 1215.

With reference now to FIGS. 4-8, exemplary embodiments of a multiple-sorter particle sorting system 1000 for a particle processing system, for example the particle processing system 100 of FIG. 1, are depicted.

As depicted in FIGS. 4-7, the multiple-sorter particle sorting system 1000 may include a first and second sort modules 1200a and 1200b arranged in parallel, for example, to the increase throughput of the particle sorting system 1000. The modules 1200a and 1200b may each include a parallel branched flow-path 1210 including a primary sensing region 1211, a sort region 1212 in proximity to the primary sensing region 1211 and a branch point 1213 downstream of the sort region 1211 where the flow-path 1210 branches into a plurality of output branch channels 1214 (also referred to herein as "individual outputs"). Notably, each output branch channel of the first sort module 1200a may merge, for example, with a corresponding output branch channel of the second sort module 1200b to form a merged output 1216 of the sort modules.

Figure 4:
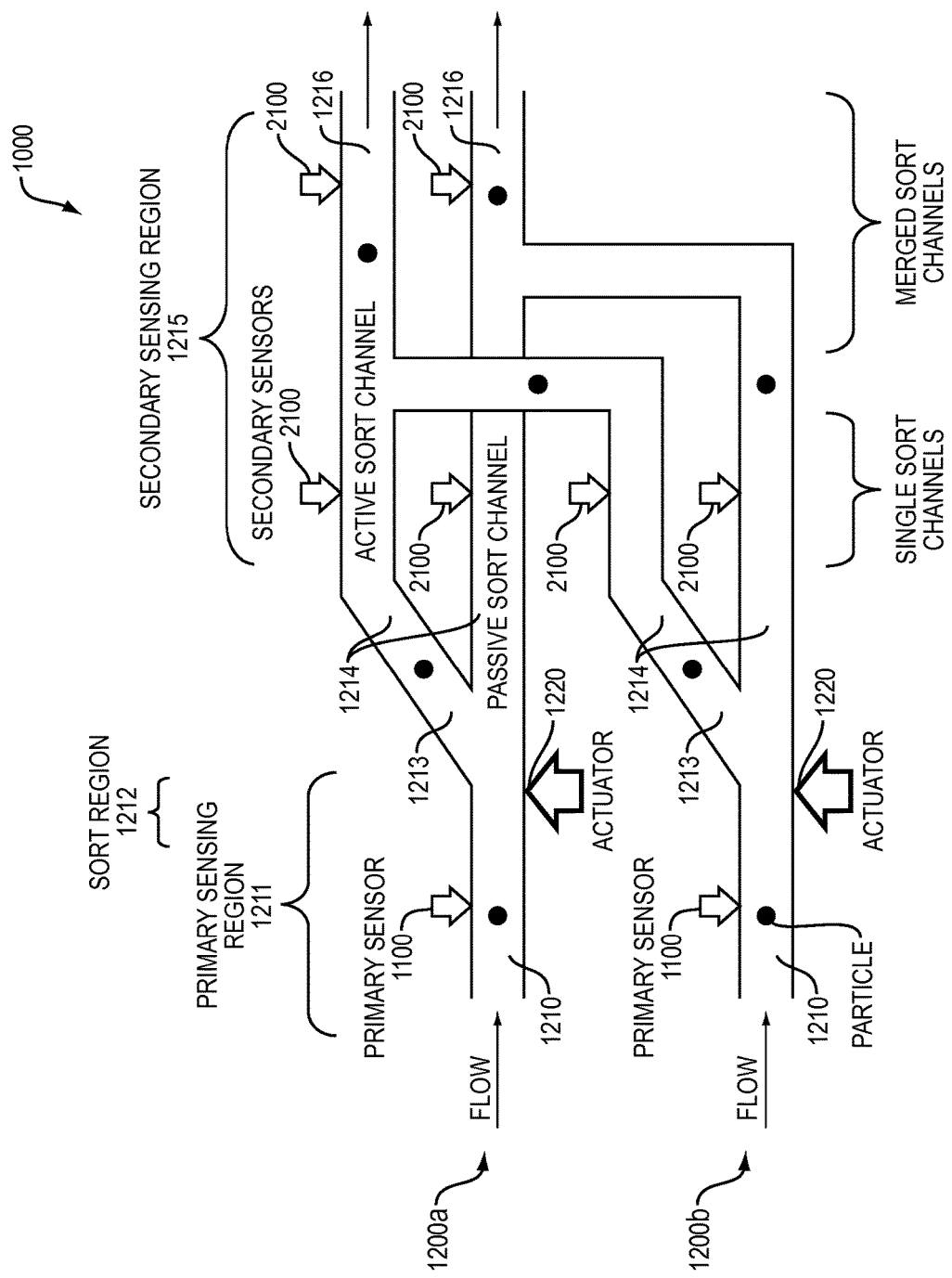
FIG. 4 depicts an exemplary multiple-sorter particle sorting system, according to the present disclosure, wherein the particle sorting system is associated with a sort monitoring system configured for monitoring particles from both individual and merged outputs of a plurality of sorters.
Figure 5:
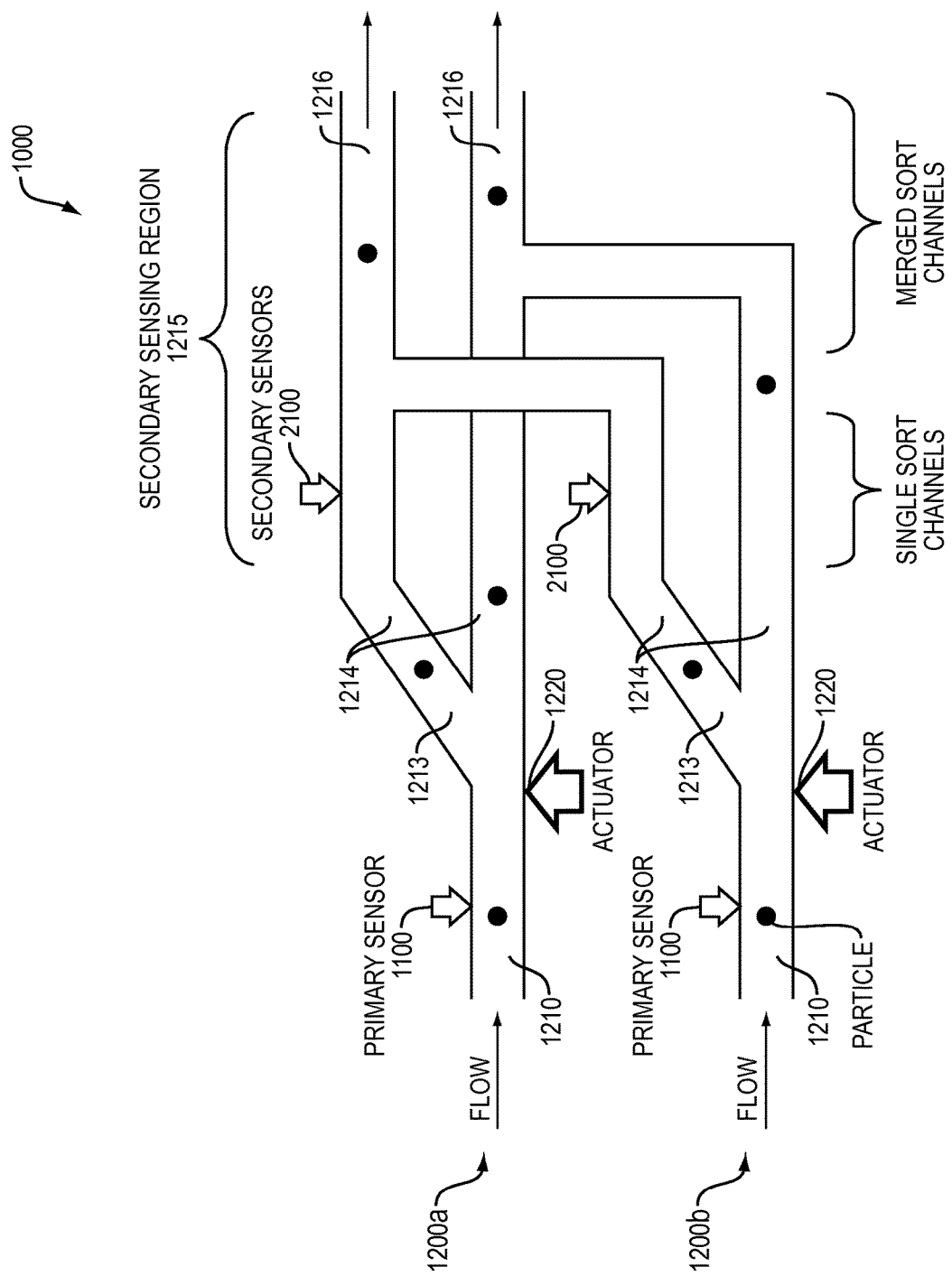
FIG. 5 depicts an exemplary multiple-sorter particle sorting system, according to the present disclosure, wherein the particle sorting system is associated with a sort monitoring system configured for monitoring particles from individual outputs of a plurality of sorters.
Figure 6:
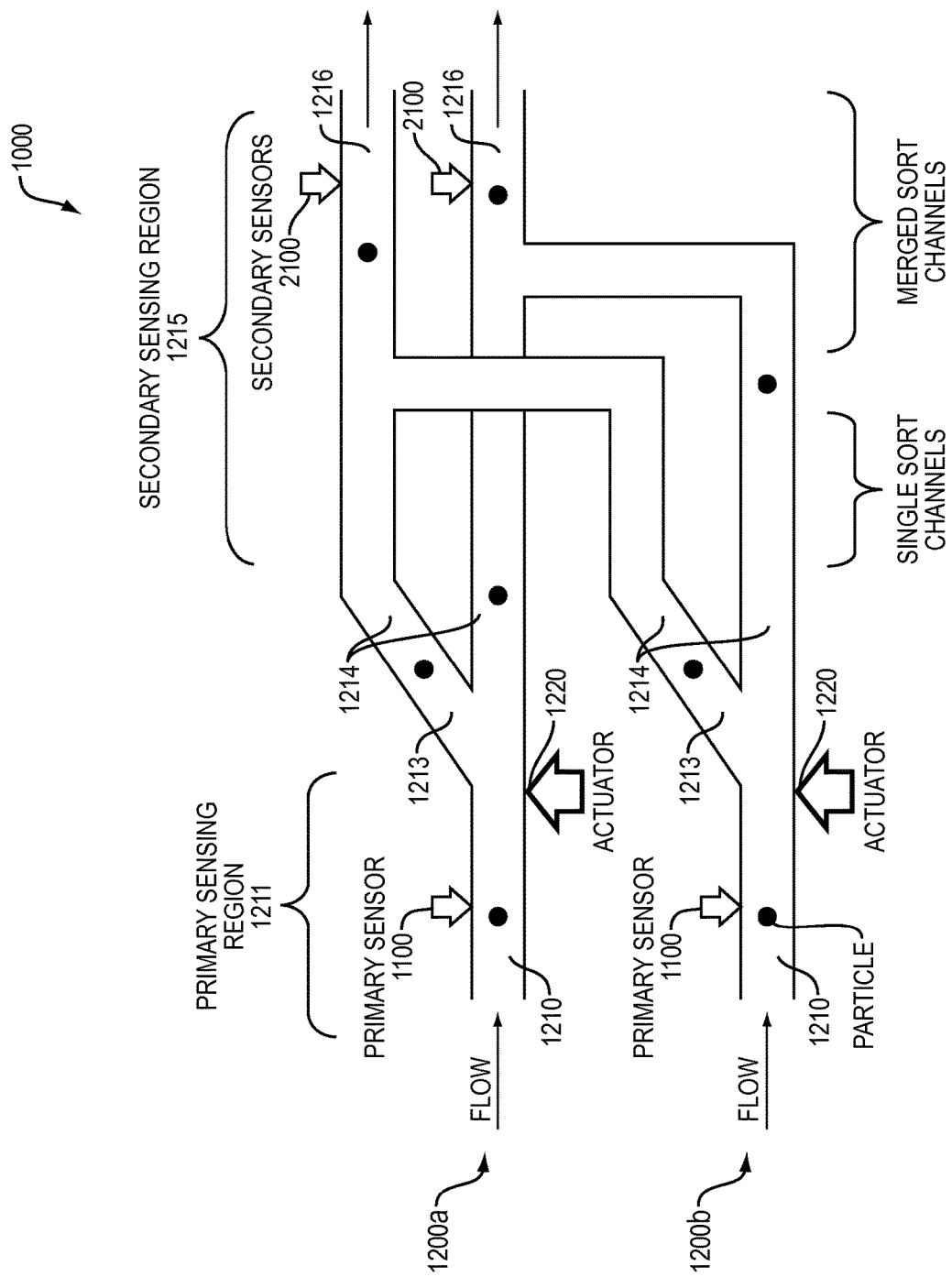
FIG. 6 depicts an exemplary multiple-sorter particle sorting system, according to the present disclosure, wherein the particle sorting system is associated with a sort monitoring system configured for monitoring particles from merged outputs of a plurality of sorters.

In exemplary embodiments, sort modules 1200a and 1200b may include or be operatively associated with one or more primary sensor systems 1100 for detecting particles at the primary sensing region 1211. In some embodiments, such as depicted in FIGS. 4-6, each sort module may include or be operatively associated with a different primary sensor system. In other embodiments, such as depicted in FIG. 7, a same primary sensor system may be configured to detect particles for both the first and second sort modules.

With reference again to FIGS. 4-7, each sort module 1200a and 1200b may include or be operatively associated with a sorter 1220 for selectively sorting particles at the sort region 1211, for example, based on prior detection of one or more predetermined characteristics, for example, by the primary sensor system(s) 1100.

Figure 7:
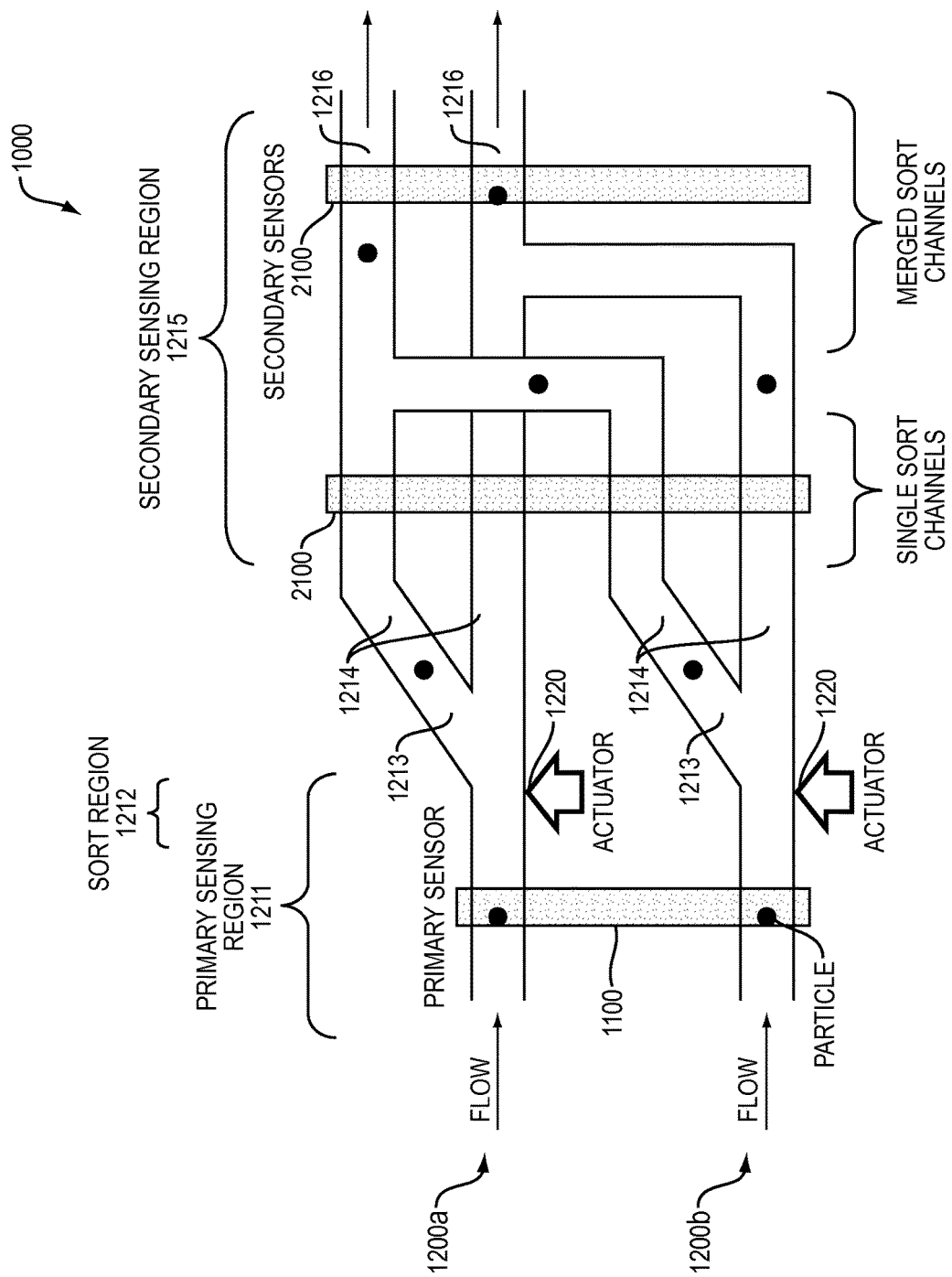
FIG. 7 depicts an exemplary embodiment of a multiple-sorter particle sorting system, according to the present disclosure, wherein a same primary sensor system is configured to detect particles for a plurality of sort modules and wherein a same secondary sensor is configured to detect particles for a plurality of sort outputs.

The particle sorting system 1000 of FIGS. 4-7 may advantageously be associated with a sort monitoring system as described herein, for example, the sort monitoring system 2000 of FIG. 1. Thus, secondary sensor systems 2100 may be used to monitor particles, for example detect a particle or an absence of a particle, at secondary detection regions 1215 downstream of the sorting of the particles by at least one of one of the sort modules 1200a and 1200b. In exemplary embodiments, the sort monitoring system may be configured to monitor particles from both individual outputs 1214 of a sort module and merged outputs 1216 of a plurality of sorter modules. For example, as depicted in FIG. 4, a secondary sensor 2100 may be included for each of the individual outputs 1214 and each of the merged outputs 1216. Alternatively, the sort monitoring system may be configured to sense or detect particles from either individual or merged outputs. For example, as depicted in FIG. 5, secondary sensor systems 2100 may be included for a corresponding pair of the individual outputs 1214 but are not included for the merged outputs 1216. Conversely, as depicted in FIG. 6, secondary sensor systems 2100 may be included for the merged outputs 1216 but not for the individual outputs 1214. In some embodiments, such as depicted in FIG. 7, a same secondary sensor may be configured to simultaneously monitor particles for a plurality of separate outputs for example, for a plurality of individual outputs 1214 or from a plurality of merged outputs 1216.

Figure 8:
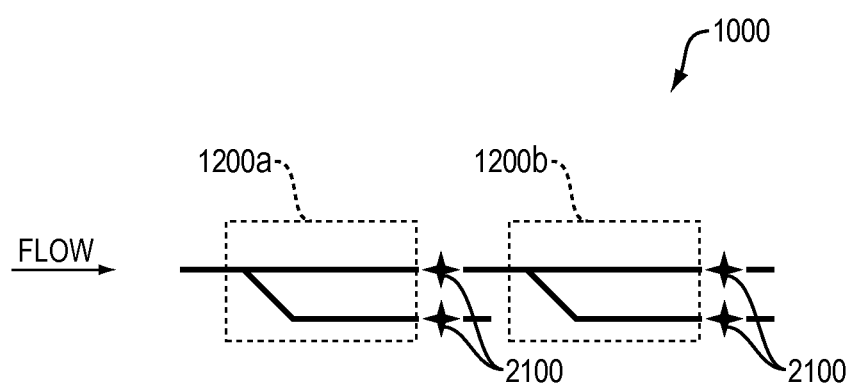
FIG. 8 depicts an exemplary multiple-sorter particle sorting system, according to the present disclosure, wherein a first sorter module is upstream of a second sorter module.

Referring now to FIG. 8, an exemplary embodiment of a multiple-sorter particle sorting system 1000 is depicted including a first sort module 1200a and a second sort module 1200b, wherein the second sort module 1200b is downstream of the first sort module 1200a. The particle sorting system 1000 of FIG. 8 may advantageously be associated with a sort monitoring system as described herein, for example, the sort monitoring system 2000 of FIG. 1. Thus, secondary sensor systems 2100 may be used to monitor particles, for example detect a particle or an absence of a particle downstream of one and/or both of the sort modules 1200a and 1200b.

Exemplary sorters and particle sorting systems are described in U.S. Pat. No. 6,808,075 and U.S. Publication No. 2010/0032350A1, which are incorporated herein in their entirety.

Figure 9C:
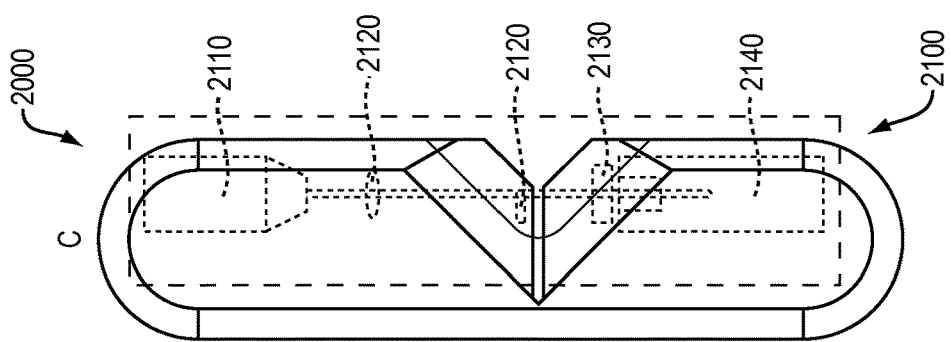
FIGS. 9a-c depict perspective, front and side schematic views, respectively, of an exemplary sort monitoring system, according to the present disclosure.
Figure 9B:
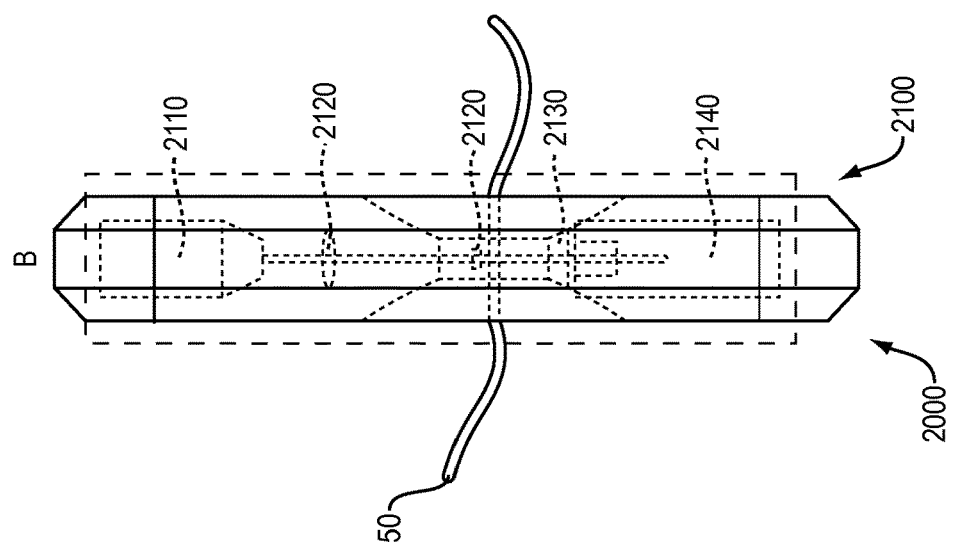
Figure 9A:
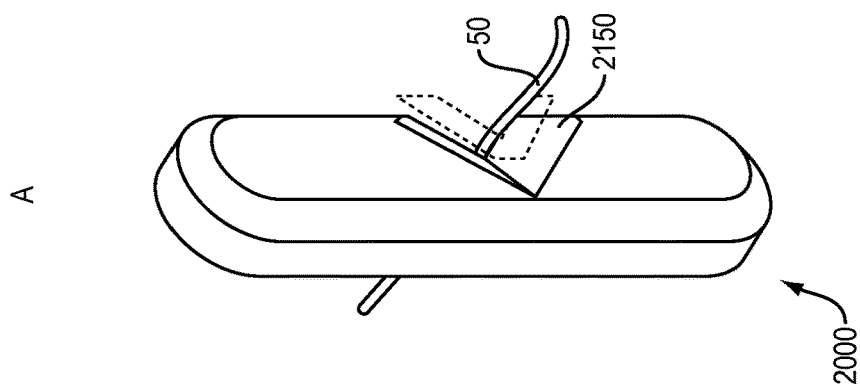

With reference now to FIGS. 9a-c, an exemplary embodiment of sort monitoring system 2000 for a particle processing system, for example the particle processing system 100 of FIG. 1, is depicted. The sort monitoring system 2000 is configurable to associate with a flow-channel/flow-path, for example, an individual output of a sort module or a merged output of a plurality of sort modules, for monitoring an operational characteristic of the sort module or the plurality of sort modules. As depicted, the sort monitoring system 2000 includes a notch or other cutout 2050 for receiving a rigid or flexible channel, for example, a capillary tube 50, connected to the flow-channel/flow-path. Thus, the exemplary sort monitoring system 2000 of FIGS. 9a-c may advantageously be a modular component, for example, a self-contained, external and/or interchangeable component, of the particle processing system. Alternatively, an exemplary sort monitoring system of the present disclosure may be integral with a particle sorting system, for example, integrated on a microfluidic chip.

Figure 11:
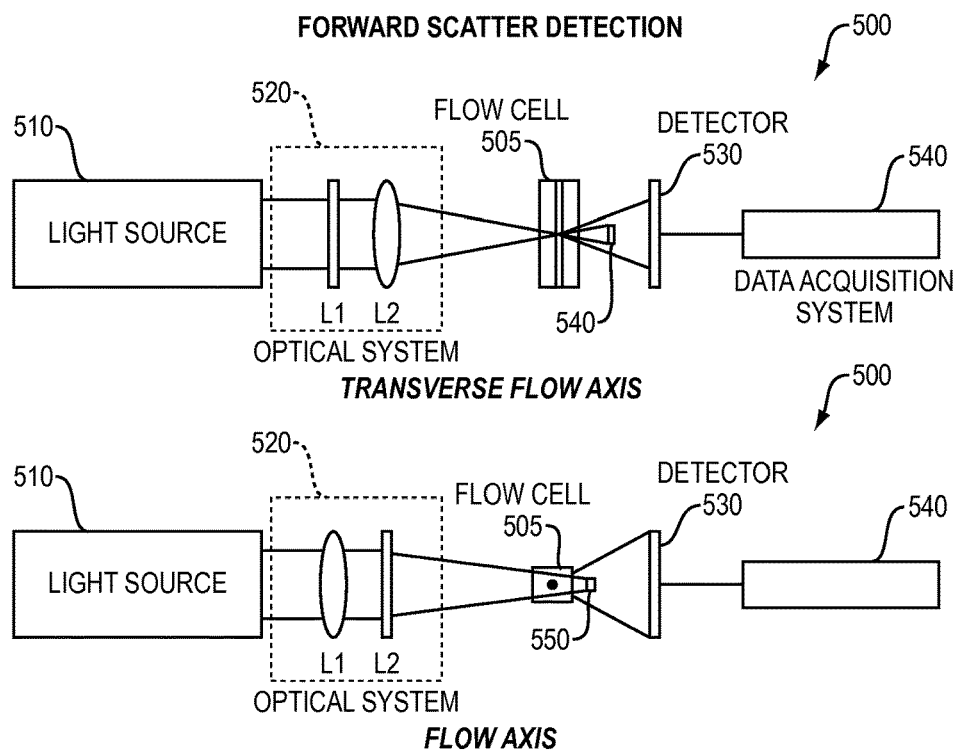
FIG. 11 depicts an exemplary optical sensor system configuration for detecting forward scatter, according to the present disclosure.
Figure 20:
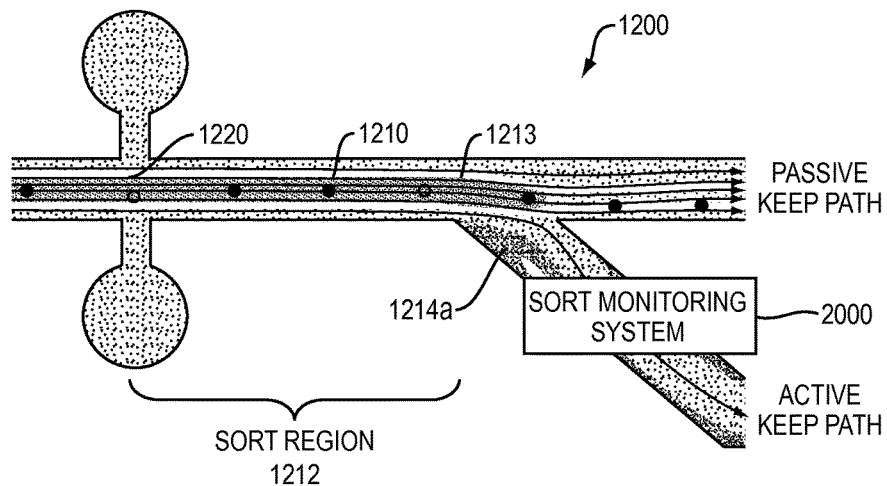
FIG. 20 depicts using an exemplary sort monitoring system to detect a baseline for an output branch of a sort channel, according to the present disclosure.

In exemplary embodiments, a sort monitoring system, for example, the sort monitoring system 2000 of FIG. 1, may be advantageously utilized to detect a baseline, for example an event rate, for an output branch, for example, an active output branch, of a sort channel. With reference to FIG. 20, an exemplary sort monitoring system 2000 may be utilized to monitor a baseline event rate for an output branch, for example, for an active output branch 1214a, of a particle processing system 1200. In exemplary embodiments, the sort monitoring system 2000 may be used to detect a particle count, for example, using an optical sensor system 500 such as depicted in FIG. 11, for the active output branch 1214a during periods of no sorting through the active output branch 1214a. In exemplary embodiments, the baseline event rate is zero or close to zero demonstrating little to no leakage between output branches.

Figure 21:
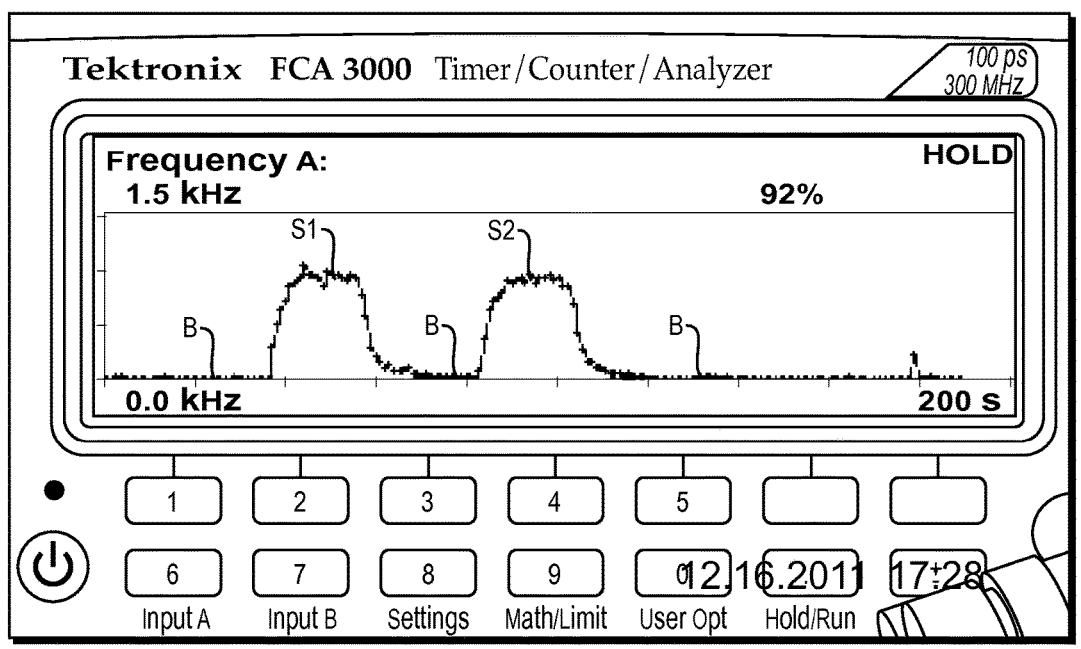
FIG. 21 depicts a counter strip chart for a particle count rate versus time of an exemplary sort monitoring system, according to the present disclosure.

In exemplary embodiments, a sort monitoring system, for example, the sort monitoring system 2000 of FIG. 1, may be advantageously utilized to detect a baseline, for example, an event rate, for a merged output of a plurality of sort modules, for example a merged output 1216 of FIG. 6. Using a 24-channel microfluidic chip (24 sort parallel modules) tests were conducted to investigate the baseline event rate for a merged output before and after sequential periods of sorting through the output branches feeding the merged output. FIG. 21 depicts a counter strip chart for a particle count rate (and therefore event rate) for the merged output during two unique periods of sorting S1 and S2 through the output branches feeding the merged output. The baseline event rate B was observed to be less than 1 Hz (1 event per second) during periods of no sorting through the output branches feeding the merged output. Once the first period of sorting S1 was initiated, the event rate was observed to increase logarithmically (due to spread of velocities and therefore observed particle concentration per unit volume of fluid downstream of sorting). During S1, sorting was maintained at approximately 1000 particles per second. After S1, sorting was halted the event rate was observed to decline exponentially again reaching the baseline event rate B as the slug of sorted particle-containing fluid exits the merged output. The second period of sorting S2 was observed to mirror the performance of S1 thus evidencing reproducibility.

Figure 16:
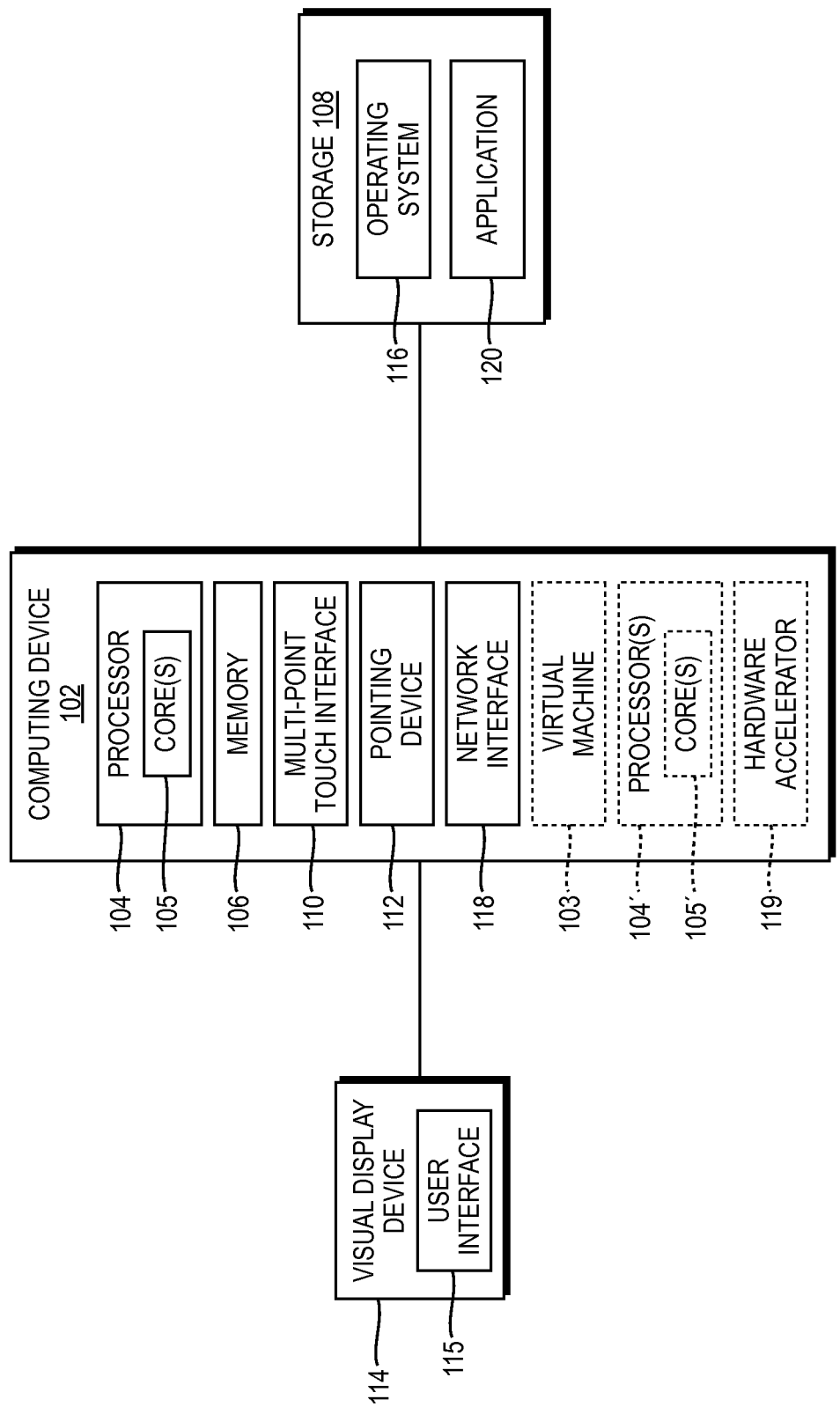
FIG. 16 depicts an exemplary computing environment according to the present disclosure.
Figure 22:
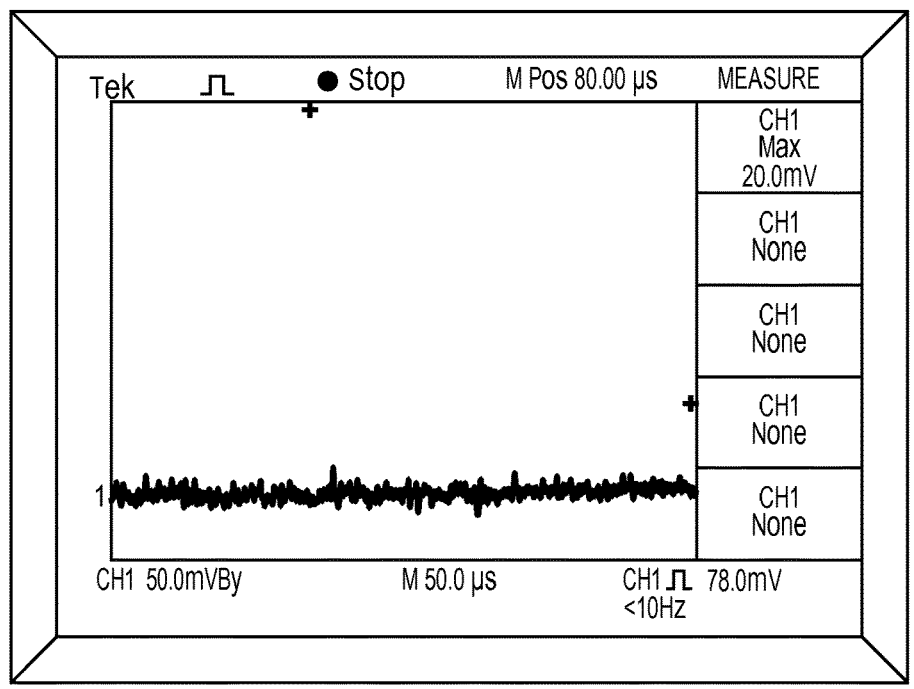
FIG. 22 depicts using an exemplary display device to display events representing instances of particles detected in an output branch during a period of no sorting through the output branch, according to the present disclosure.
Figure 23:
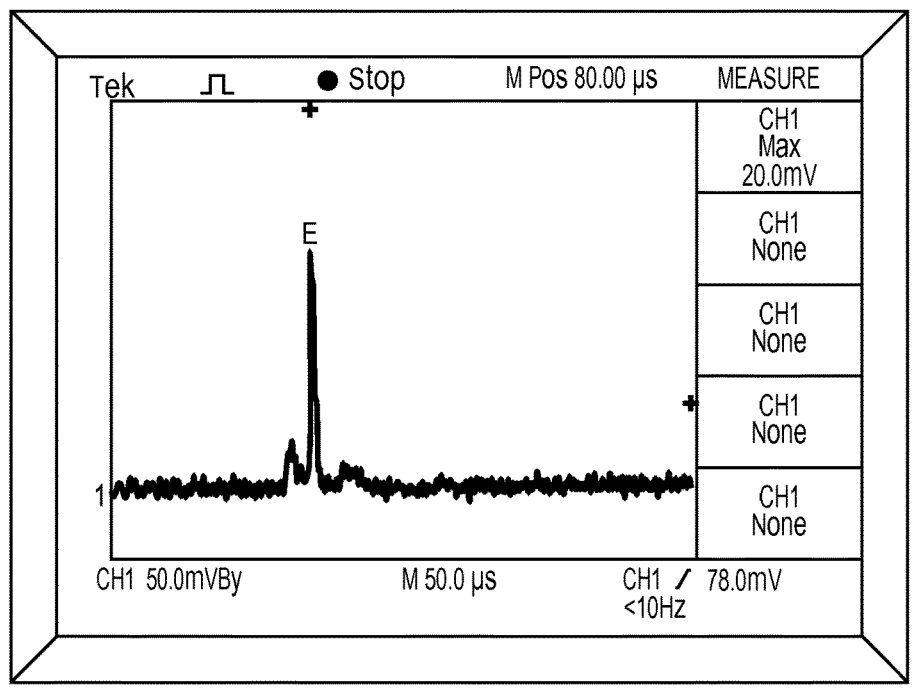
FIG. 23 depicts an exemplary outlier event as observed using an exemplary display device to monitor events representing instances of particles detected in an output branch, during a period of no sorting through the output branch according to the present disclosure.
Figure 24:
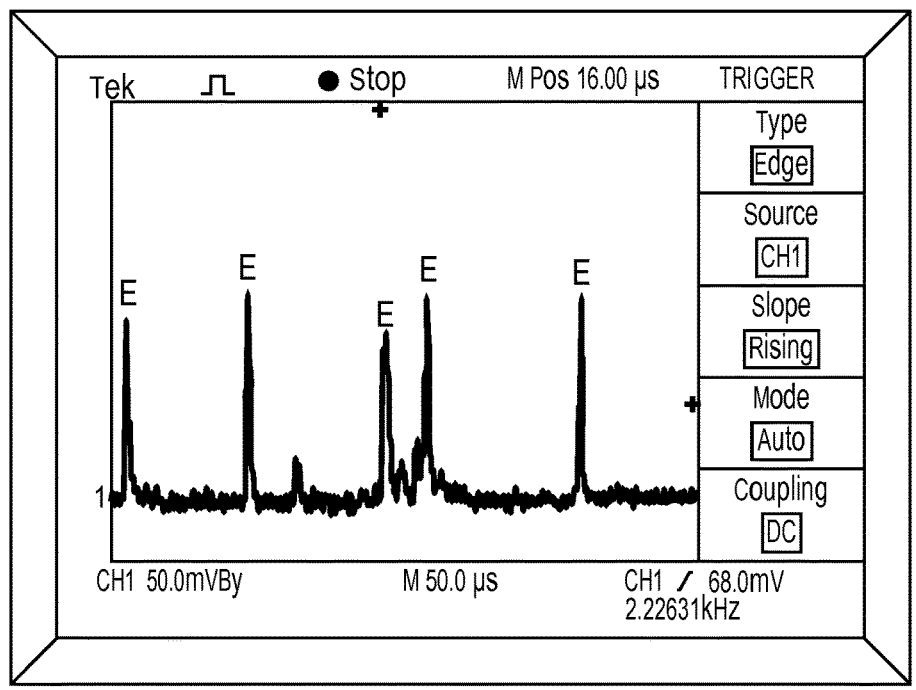
FIG. 24 depicts using an exemplary display device to display events representing instances of particles detected in an output branch during a period of sorting through the output branch, according to the present disclosure.
Figure 25:
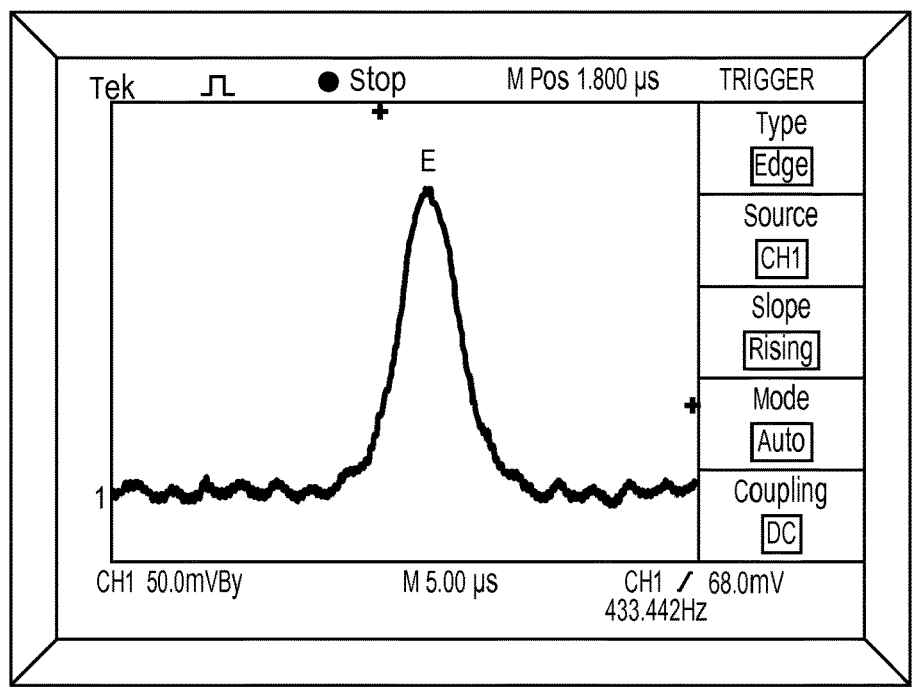
FIG. 25 depicts a zoomed in view of an exemplary event observed using an exemplary display device to monitor events representing instances of particles detected in an output branch during a period of sorting through the output branch, according to the present disclosure.

In exemplary embodiments a visual display device, for example, visual display device 114 of FIG. 16, may be used to monitor in real time or near real time an event rate, for example, a baseline event rate such as event rate B of FIG. 21, for a sort channel and/or an output branch thereof. FIGS. 22-25, depict using an exemplary display device 114 to monitor events representing instances of particles detected in an active output branch. As depicted in FIG. 22, an absence of events is depicted a during period of no active sorting through the active output branch. Any observed event E in the active output branch during a period of no active sorting through the active output branch (see FIG. 23) is likely an outlier representing, for example, a residual or carry-over particle such as from a prior period of sorting through the active output branch. It is noted that in the event that As depicted in FIG. 24 a much higher frequency of events E is observed during a period of sorting through the active output branch. FIG. 25 depicts a zoomed in view of one of the observed events E in FIG. 24. Based on the frequency of events during periods of sorting and no sorting through an active output branch, a baseline margin of error for sort rate may be determined. Notably, the greater the sort rate during active sorting through the active output branch the lower the baseline margin of error. In experiments conducted using a 24 channel microfluidic sorter chip, particles were sorted over a range of actuation rates from less than 0.01 to over 5 kHz to test the dynamic range of the system.

Sensor systems, according to the present disclosure, for example primary and secondary sensor systems, may be any sensor system for monitoring a particle including but not limited to optical sensor systems, electrical sensor system, magnetic sensor system, acoustic sensor systems and the like. Sensor systems may advantageously be used to detect a particle or an absence of a particle in a flow-channel/flow-path, for example, based on light intensity observed through one or more pin holes. Sensor systems may further be used to detect one or more particle characteristics, for example, for facilitating identification/classification of particles.

Exemplary optical sensor system configurations are provided in FIGS. 10-13. In general, these configurations involve electromagnetic radiation illumination of particles in a flow-channel/flow-path 505, for example, using a coherent or incoherent light source with or without additional light focusing elements, and the detection of light interaction (scatter, absorption, extinction, reflection, refraction, diffraction, fluorescence, plasmonic) in one or more directions. As depicted, each configuration includes a light source 510 (which may be a coherent light source, for example, a laser or an incoherent light source, for example, a light emitting diode), focusing optics 520 (for example single or multiple refractive, reflective, diffractive and or fiber optic elements) and an optical sensor 530 (for example, a photodiode, photomultiplier tube, pyroelectric detector, bolometer, APD, multiple-pixel photon counter, or CCD array). In exemplary embodiments, the monitoring system configuration may include or be operatively associated with a data acquisition system 540, to count the number and/or monitor the magnitude of the electrical pulses produced by the sensor 530. Pulse detection may be performed with analog circuitry, for example, a threshold detector, or digital circuitry, for example, an A/D converter, or digital counting circuitry. A programmable processor may then be used to display, analyze, and document the enumeration results, for example in order to detect a presence or an absence of particle or identify/classify a particle.

Figure 10:
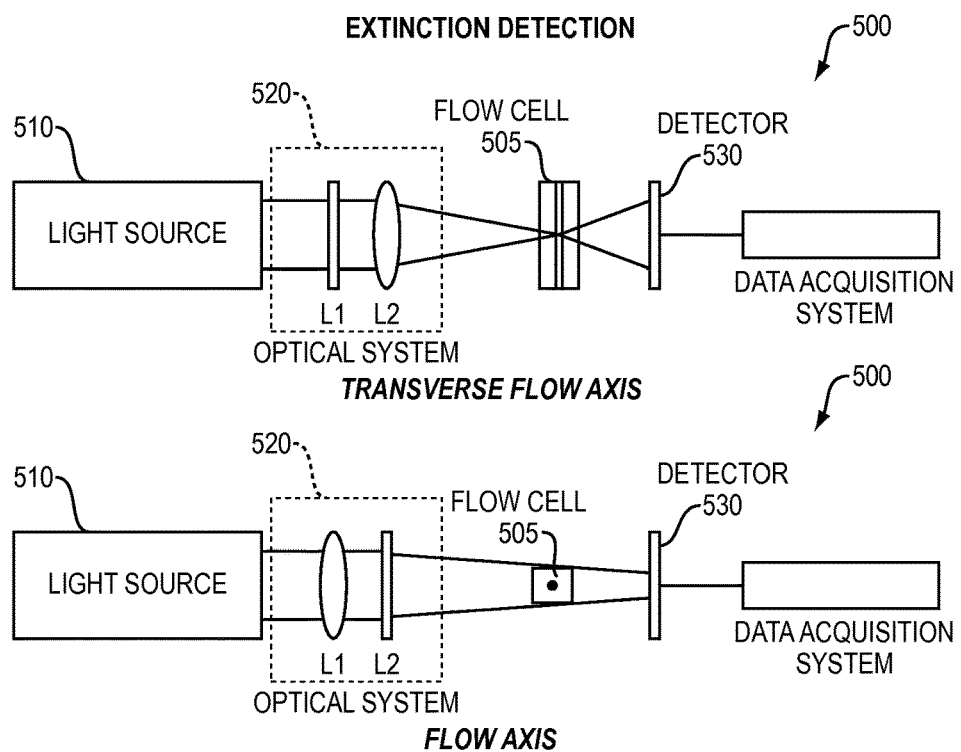
FIG. 10 depicts an exemplary optical sensor system configuration for detecting extinction, according to the present disclosure.

With specific reference to FIG. 10, traverse flow axis and flow axis views of an exemplary configuration for an optical sensor system 500 are depicted, wherein particle detection is measured by the amount of light attenuated by a particle that traverses an optical beam that intersects the fluidic stream. The optical sensor 530 of the optical sensor system configuration depicted in FIG. 10 may be sensitive to extinction signal levels generated by a particle and may typically be positioned to collect light substantially in line with the illumination axis of the light source 510. It is noted that in other exemplary embodiments the optical sensor 530 may be positioned to collect light at different angles relative to the illumination axis (see, for example FIG. 13). The exemplary sort monitoring system 2000 depicted in FIG. 9 may include a monitor sensor system 2100 with a similar configuration to optical sensor system configuration depicted in FIG. 10 (for example, the monitor sensor system 2100 includes a light source 2110, focusing optics 2120, an optical detector 2130 and a data acquisition system 2140).

With specific reference to FIG. 11, traverse flow axis and flow axis views of an exemplary configuration for an optical sensor system 500 are depicted, wherein particle detection measured by the amount of light scattered in the forward direction by a particle that traverses an optical beam that intersects the fluidic stream. The optical sensor 530 of the optical sensor system configuration depicted in FIG. 11 may be sensitive to forward scatter signal levels generated by a particle and may typically be positioned to collect light substantially in line with the illumination axis of the light source 510. It is noted that in other exemplary embodiments, the optical sensor 530 may be positioned to collect light at different angles relative to the illumination axis (see, for example FIG. 13). The optical sensor system 500 of FIG. 11 may include an obscuration element 550, such as an obscuration disk, obscuration bar, obscuration mask, or the like, for blocking direct illumination light exiting the flow-channel/flow-path 505 from entering the sensor 530. The detection angle of the sensor 530 may be larger than the obscuration angle of the illumination beam. In exemplary embodiments, a lens system may be included in between the flow-channel/flow-path 505 and the detector to maximize scattered light collection from the particle.

Figure 12:
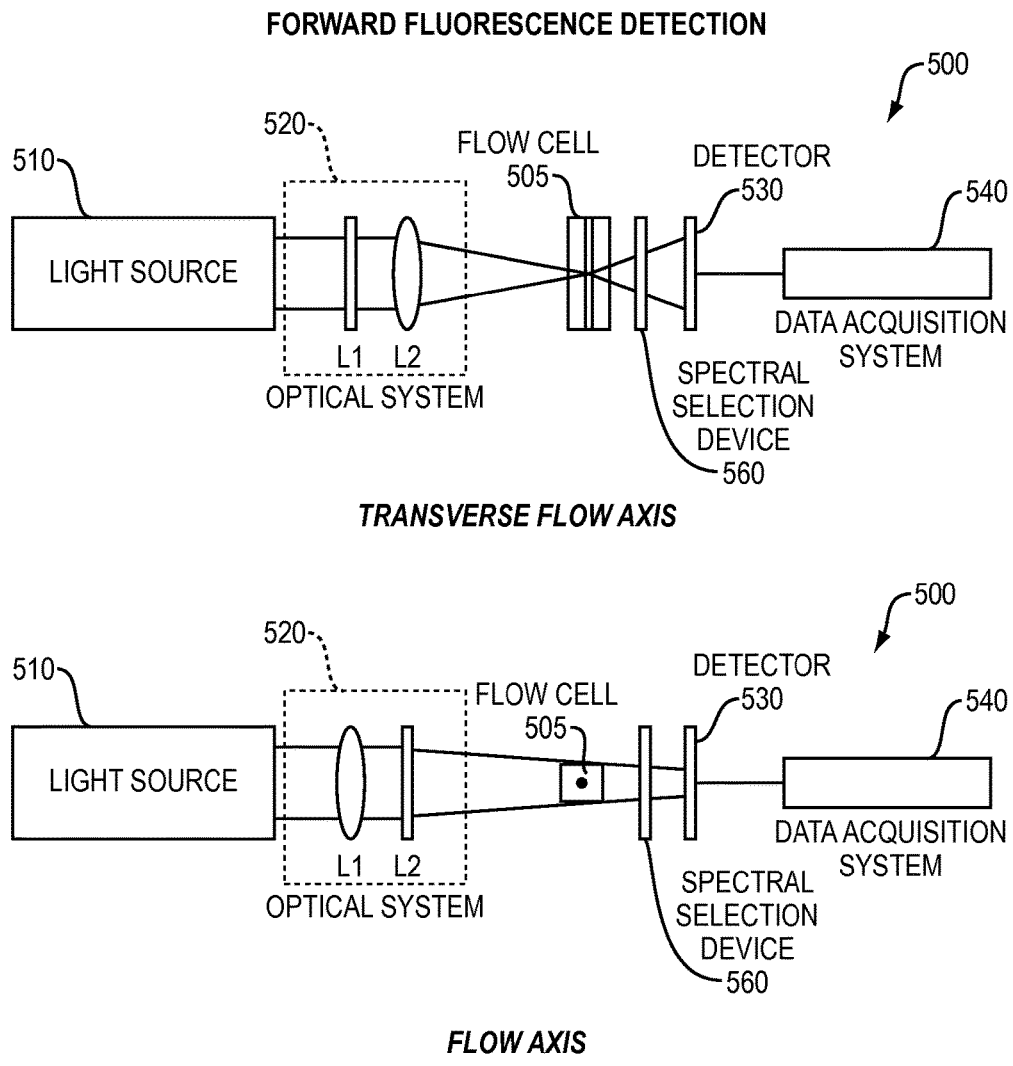
FIG. 12 depicts an exemplary optical sensor system configuration for detecting forward florescence, according to the present disclosure.

With specific reference to FIG. 12, traverse flow axis and flow axis views of an exemplary configuration for an optical sensor system 500 are depicted, wherein particle detection is measured by the amount of fluorescent light emitted by a particle excited by an optical beam. As depicted, the fluorescence detection angle is in the forward direction relative to the excitation beam. The optical sensor 530 of the optical sensor system configuration depicted in FIG. 12 may typically be positioned to collect light substantially in line with the illumination axis of the light source 510. It is noted that in other exemplary embodiments, the optical sensor 530 may be positioned to collect light at different angles relative to the illumination axis (see, for example FIG. 13). In exemplary embodiments, a detected particle may be labeled with a fluorophore to enhance fluorescence detection. Otherwise, detection of intrinsic autofluorescence from the particle may be used. The optical sensor system 500 of FIG. 12 may include a spectral selection component 560, for example, a refractive, diffractive, or interference filter or other spectrally selective element, between the flow-channel/flow-path 505 and the sensor 530 to select an optimal spectral range for fluorescent light emitted by a particle, and to attenuate excitation light from entering the sensor 530. In exemplary embodiments, a second spectral selective component may be placed in between the light source 510 and the flow-channel/flow-path 505 configured to select an optimal spectral range for fluorescence excitation.

Figure 13:
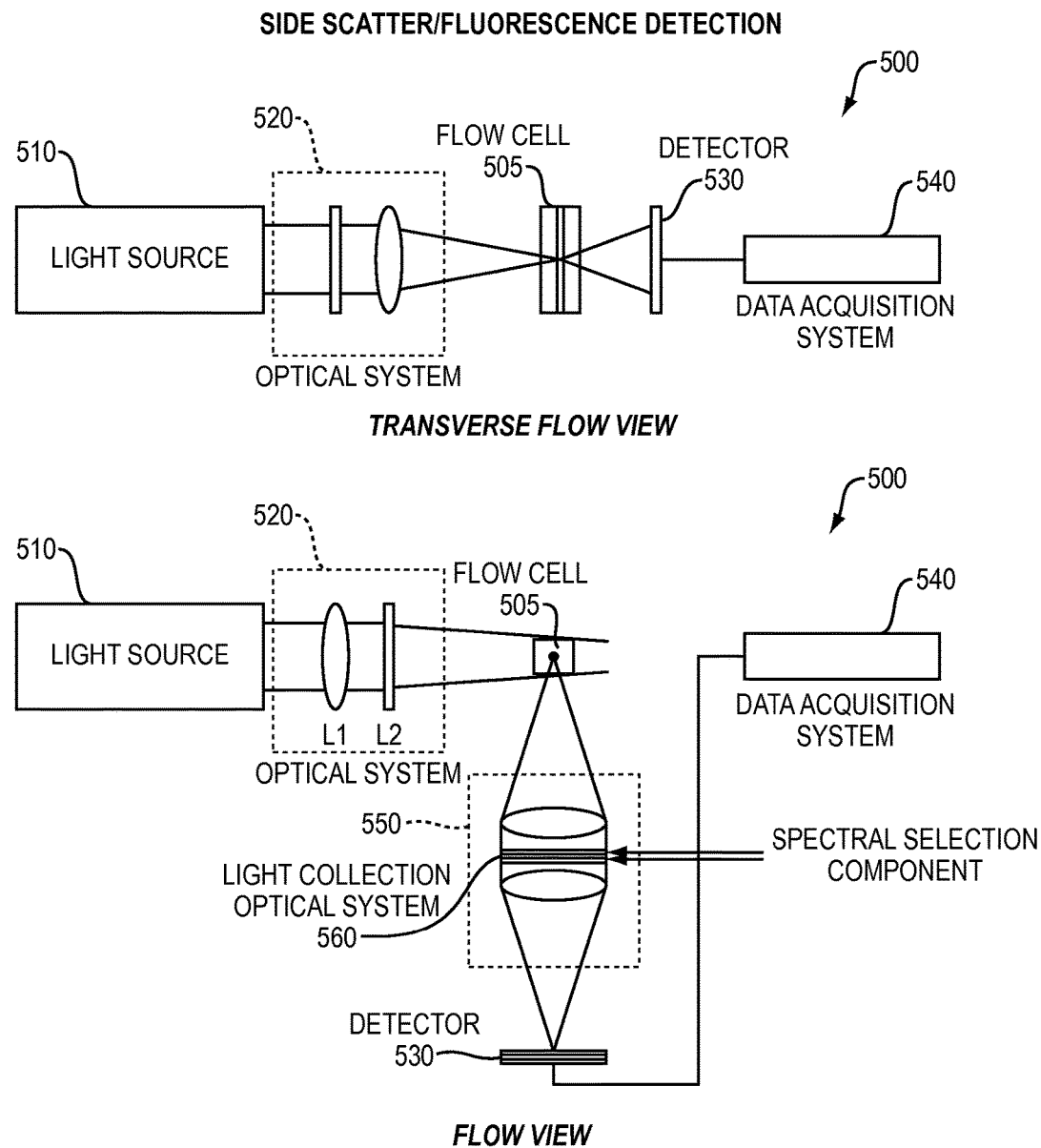
FIG. 13 depicts an exemplary optical sensor system configuration for detecting side scatter and/or side florescence, according to the present disclosure.

With specific reference to FIG. 13, traverse flow axis and flow axis views of an exemplary configuration for an optical sensor system 500, wherein particle detection is measured by side scatter or side florescence. The optical sensor 530 of the optical sensor system configuration depicted in FIG. 13 may typically be positioned to collect light at an angle to the illumination axis, for example, substantially orthogonal to the illumination axis.

In the case of scatter detection, the optical sensor system 500 of FIG. 13 may include, an obscuration element 550 for blocking direct illumination light exiting the flow-channel/flow-path 505 from entering the sensor 530. The detection angle of the sensor 530 may be larger than the obscuration angle of the illumination beam. In exemplary embodiments involving scatter detection, a lens system may be included in between the flow-channel/flow-path 505 and the detector to maximize scattered light collection from the particle.

In the case florescence detection, the optical sensor system 500 of FIG. 13 may include a spectral selection component 560, for example, a refractive, diffractive, or interference filter or other spectrally selective element, between the flow-channel/flow-path 505 and the sensor 530 to select an optimal spectral range for fluorescent light emitted by a particle, and to attenuate excitation light from entering the sensor 530. A second spectral selective component may be placed in between the light source 510 and the flow-channel/flow-path 505 configured to select an optimal spectral range for fluorescence excitation.

As noted above, sensor system configurations are not limited to optical configurations. Indeed, other sensing approaches may be applied instead of or in conjunction with optical means. These sensing approaches may include but are not limited to (i) passive or active electrical detection including but not limited to conductance, capacitance, RF field monitoring through devices fabricated on the microchip, or located off-chip near channels of interest (ii) magnetic detection, such as using a Hall-effect device or other field probes located in the proximity of flow-channels and (iii) acoustic detection such as ultrasound absorption, reflection, scatter or the like using on-board or remote devices. Other optomechanical or electromagnetic sensing systems may also be employed.

In exemplary embodiments, a particle may be detected by an analog level, for example by surpassing (going above or below) a threshold which produces a detectable voltage change. The signal may be used to characterize, identify or count the particle. Temporal information may be used to determine the velocity of the particle, the time elapsed from the detection of the particle at another location, the expected time that the particle will reach a selected position, or the like.

In exemplary embodiments, conductive traces may be used to form an electrode array across or along one or more flow paths where the absence or presence of a particle adjusts the conductivity or other electrical measurement, for example, capacitance, resistance, inductance of the fluid path between any electrode pair. The conductive traces may be formed on one substrate of a microfluidic chip prior to fusing a second substrate to provide contact with flow path. As a particle flows near or between electrodes, the conductivity of electricity of the electrical circuit may change and be detected with appropriate electronic processing tools such as an analog current meter or a computer.

Figure 14:
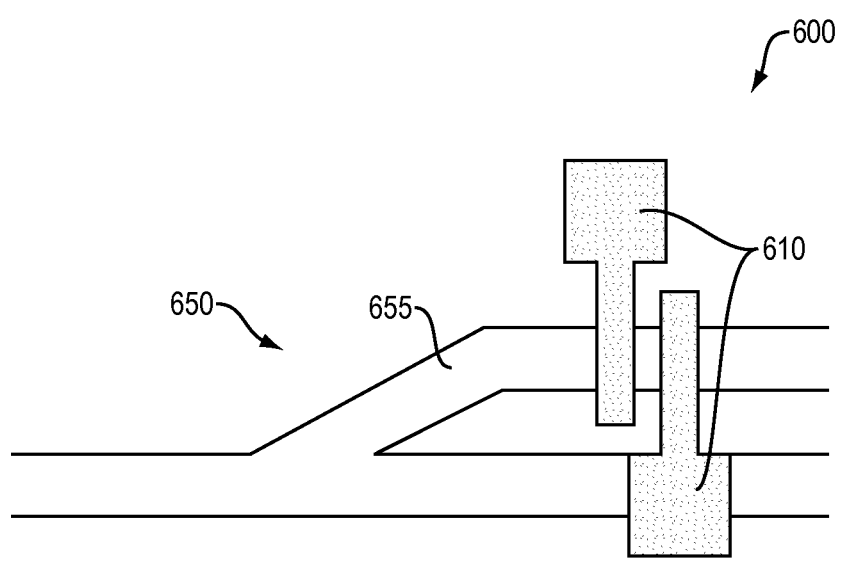
FIG. 14 depicts an exemplary electrode for detecting particles in an output branch channel of a sort module, according to the present disclosure.

Referring now to FIG. 14, an exemplary electrode array 600 is depicted. The electrode array 600 includes a pair of conductive traces 610 which may be operatively associated with, for example, electrically coupled to, an electric property detector such as a current meter, capacitance meter, ohm meter, inductance meter, multi-meter, or the like. Electric properties which may be detected include but are not limited to conductivity, capacitance, resistance, inductance, and the like. As depicted the electrode array 600 includes a pair of conductive traces 610 associated with a channel or channels. For example, the conductive traces 610 may be positioned adjacent or across a channel. In exemplary embodiments the conductive traces 610 may be associated with, one, two or all output branch channel(s) (for example, output branch channel 655) of a sort module 650. Thus, a particle or an absence of a particle in a channel, for example in the output branch channel 655, may be detected by monitoring changes in electric properties of the array 600 such as changes in changes in electric properties between the traces 610. In some embodiments, the array 600 includes a plurality of conductive trace pairs. In some embodiments, a first of the plurality of conductive trace pairs are configured to detect or measure a first selected electric property of a particle and a second of the plurality of conductive trace pairs is configured to detect or measure a second selected electric property of a particle.

In exemplary embodiments, the electrode array 600 may be associated with active and/or a passive output branch channels of the sort module 650. The electrode array 600 may further be associated with output branch channels of a plurality of sort modules. In some embodiments, the electrode array 600 may include a plurality of pairs of conductive traces each associated with a different channel, for example a different output branch channel of a sort module 650 or a plurality of sort modules. In other embodiments, in order to conserve space, the electrode array may include a pair of conductive traces associated with a plurality of channels, for example, a plurality of output branch channels of a sort module 650 or sort modules. In some embodiments, the electrode array may include a pair of conductive traces associated with a plurality of passive output branch channels of a sort module 650 or sort modules. In other embodiments, the electrode array may include a pair of conductive traces associated with a plurality of active output branch channels of a sort module 650 or sort modules. In exemplary embodiments where the electrode array includes a pair of conductive traces associated with a plurality of channels, channels may be distinguished, for example, based on particle spacing/timing and/or modulation signatures for different channels.

Figure 15:
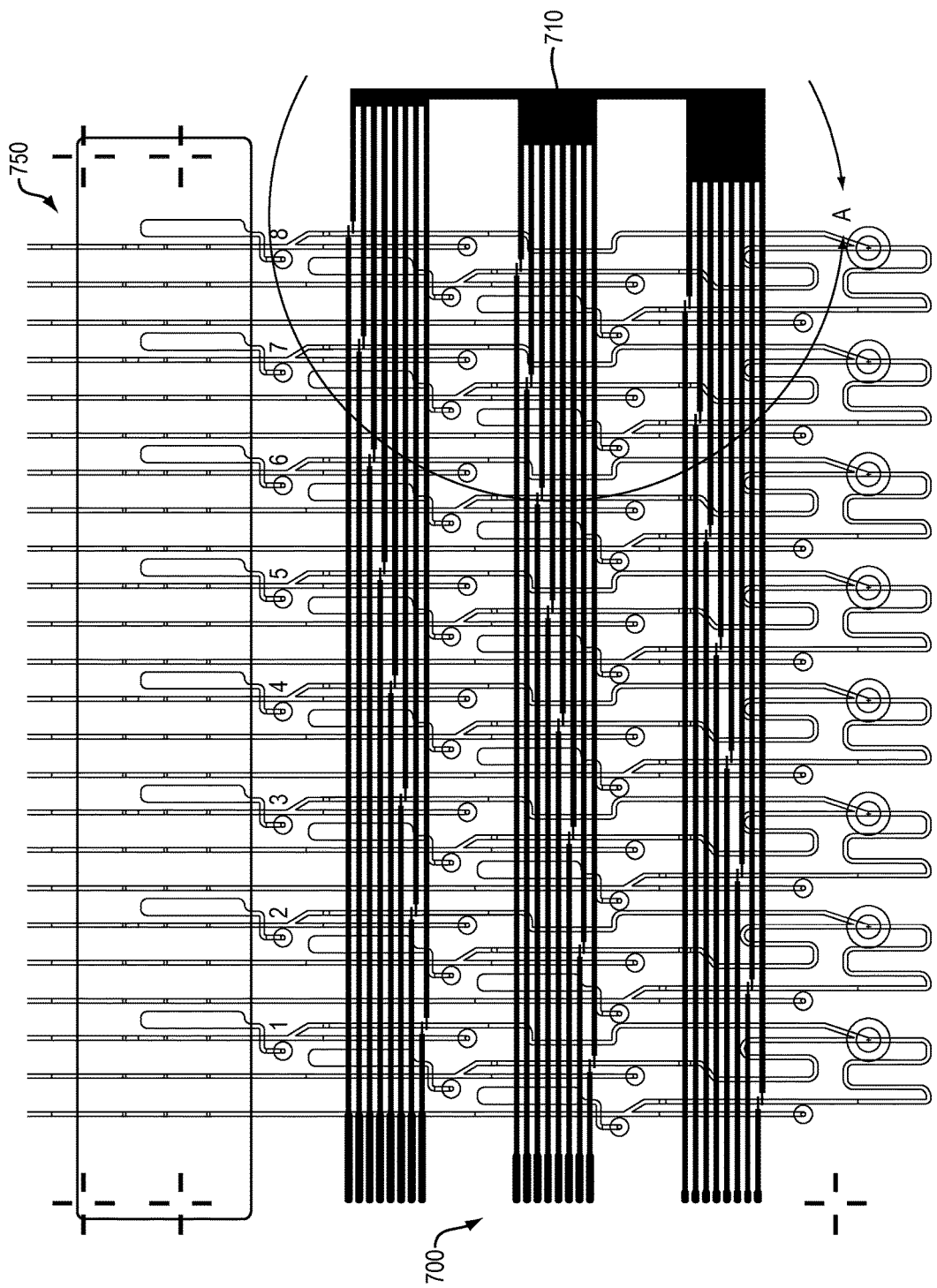
FIG. 15 depicts an exemplary electrode array for detecting particles in multiple output branch channels of a multi-sorter system, according to the present disclosure.

Referring now to FIG. 15, an electric array 700 may be adapted detect particles in multiple output branch channels of a particle sorting system 750. Thus, the electric array 700 may include a plurality of pairs of conductive traces, e.g., wherein one or both traces for each pair are independently coupled to a detector for detecting an electric property, for example, across a corresponding one of the output branch channels. Advantageously one trace in each pair may share a common ground 710.

The monitor system configurations and sensing approaches described may be applied for both modular and integrated embodiments of the sort monitoring system. It will be appreciated by one of ordinary skill in the art that particle detection may be measured by any combination of sensor configurations. The use of multiple parameter detection may advantageously enable detection of subpopulations of sorted particles.

In exemplary embodiments, the sort monitoring system of the present disclosure may be used to monitor and, in some instances, evaluate and/or control, a baseline presence/absence of microparticles for an output of a sort module or a group of sort modules for a given sorter state. Baseline monitoring may be established before, during, between, or after sorting functions. Sorting conditions may then be adjusted to regulate the baseline, for example, for a selected sort mode such as purification, recovery, enrichment, or the like. Baseline monitoring may also be used to determine whether a sort may begin, continue or halt, or whether additional actions may be required (for example a cleaning step).

The sort monitoring system of the present disclosure may also be used to count (instead of or in addition to detecting a particle characteristic, for example size, velocity, position, time or flight, granularity, light scatter, fluorescence, magnetism, conductivity, capacitance, acoustic properties, or the like) the number of particles (sorted or otherwise) for one, many, or all outputs, including individual and merged outputs, of a sort module or a group of sort modules. A monitored particle count may then be compared to an expected particle count, for example, post-sort particle counts may be compared to pre-sort particle counts. The sort monitoring system may be used to determine, for example, actual versus expected sort rate, quantity, quota (i.e. if sufficient particles of a particular type have been isolated, and measured to have been isolated) and other sort statistics/information. The sort monitoring system may further be configured to identify and, in some instances, track one, many, or all particles that flow through the particle sorting system, for example, to aid in monitoring production/processing of multiple sort samples from a single input sample, to verify marking of a particle (changing the state of a particle as part of the sort operation), or to estimate and or determine a composition of a sample that has been processed by a particle sorting system.

Various operational characteristics of a particle processing system may be controlled based on the sort monitoring system. The sort monitoring system may be configured to begin, continue or halt, a sorting operation or take an additional action (for example a cleaning step) based on a monitored operational characteristic. In multiple-channel and multiple-sorter systems, sorter operations in a selected flow-channel/sort module may be adjusted (while other flow-channels/sort modules remained unaffected).

In exemplary embodiments, the sort monitoring system may be configured to adjust a sample introduction rate and/or fluid flow into a sort module or a group of sort modules, for example, to ensure optimal sort performance throughout a sort. For example if a particle sorting system is overperforming, in terms of accuracy, the sort monitoring system may be configured to increase throughput, for example, by increasing sample introduction rate and/or fluid flow. Conversely, if the particle processing system is underperforming in terms of accuracy, for example, due to sort timing errors resulting from false or missed sort, the sort monitoring system may be configured to decrease sample introduction rate and/or fluid flow thereby reducing the incidence of coincidence events. The particle processing system may also be configured to calibrate/optimize the delay timing calculation based on the detection of coincidence events.

In exemplary embodiments, as noted above, a sorting system may be configured to simultaneously sort multiple samples (sources) and/or utilize multiple sorters, for example, within a single microfluidic substrate. The sort monitoring system of the present disclosure may be configured to monitor individual performance of one, many or all sorters/flow-channels and/or combined performance of a plurality of sorters/flow-channels. This versatility is particularly useful for monitoring sorters/flow-channels tasked with different operating criteria/conditions and for managing multiple-sorter/channel systems. For example, a combined performance of a multiple-channel system may serve as a preliminary threshold, for example, to determine whether to take an action such as halting one of the sorters/flow-channels. Individual performances of each flow-channel may then be used to assess which of the channel or channels to act upon. In this way, flow-channels with superior performance compensate for flow-channels with inferior performance (provided that the combined output is within acceptable tolerances) and a high throughput is maintained.

In exemplary embodiments, the sort monitoring system may be used to monitor/optimize a multiple-particle distribution (population statistics). The sort monitoring system may be configured to monitor/adjust a sort fraction in real-time. Optimal operational conditions for a desired sort fraction may also be stored for future use.

As noted above, the sort monitoring system of the present disclosure is able to provide knowledge of the yield, number, recovery and purity of particles after the sorting thereof. The sort monitoring systems allows for efficient use of precious sample, instrument time, user time, consumable materials and other resources. For example, the sort monitoring system may be used to notify a user when a particular number of particles are isolated or to maximize a number of sorted samples from a single input for multiple-treatment or multiple-patient use. This is particularly, useful when dealing with precious, rare or high-value materials or when a subsequent step needs to be performed on a sorted fraction.

It is explicitly contemplated that the systems and methods presented herein may include one or more programmable processing units having associated therewith executable instructions held on one or more computer readable medium, RAM, ROM, harddrive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

Displays and/or other feedback means may also be included to convey detected/processed data. In exemplary embodiments, notifications may be displayed, for example, on a monitor. The display and/or other feedback means may be stand-alone or may be included as one or more components/modules of the processing unit(s). In exemplary embodiments, the display and/or other feedback means may be used to facilitate selection of one or more suggested actions based a detected operational characteristic of a particle sorting system.

The actual software code or control hardware which may be used to implement some of the present embodiments is not intended to limit the scope of such embodiments. For example, certain aspects of the embodiments described herein may be implemented in code using any suitable programming language type such as, for example, assembly code, C, C# or C++ using, for example, conventional or object-oriented programming techniques. Such code is stored or held on any type of suitable computer-readable medium or media such as, for example, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include storage medium for storing software, including a hard disk, an optical disk, floppy disk, ROM (read only memory), RAM (random access memory), PROM (programmable ROM), EEPROM (electrically erasable PROM), flash memory storage devices, or the like.

Referring now to FIG. 16, an exemplary computing environment suitable for practicing exemplary embodiments is depicted. The environment may include a computing device 102 which includes one or more media for storing one or more computer-executable instructions or code for implementing exemplary embodiments. For example, memory 106 included in the computing device 102 may store computer-executable instructions or software, for example instructions for implementing and processing every module of the application 120.

The computing device 102 also includes processor 104, and, one or more processor(s) 104' for executing software stored in the memory 106, and other programs for controlling system hardware. Processor 104 and processor(s) 104' each can be a single core processor or multiple core (105 and 105') processor. Virtualization can be employed in computing device 102 so that infrastructure and resources in the computing device can be shared dynamically. Virtualized processors may also be used with application 120 and other software in storage 108. A virtual machine 103 can be provided to handle a process running on multiple processors so that the process appears to be using one computing resource rather than multiple. Multiple virtual machines can also be used with one processor. Other computing resources, such as field-programmable gate arrays (FPGA), application specific integrated circuit (ASIC), digital signal processor (DSP), Graphics Processing Unit (GPU), and general-purpose processor (GPP), may also be used for executing code and/or software. A hardware accelerator 119, such as implemented in an ASIC, FPGA, or the like, can additionally be used to speed up the general processing rate of the computing device 102.

The memory 106 may comprise a computer system memory or random access memory, such as DRAM, SRAM, EDO RAM, or the like. The memory 106 may comprise other types of memory as well, or combinations thereof. A user may interact with the computing device 102 through a visual display device 114, such as a computer monitor, which may display one or more user interfaces 115. The visual display device 114 may also display other aspects or elements of exemplary embodiments, for example, notifications. The computing device 102 may include other I/O devices such a keyboard or a multiple-point touch interface 110 and a pointing device 112, for example a mouse, for receiving input from a user. The keyboard 110 and the pointing device 112 may be connected to the visual display device 114. The computing device 102 may include other suitable conventional I/O peripherals. The computing device 102 may further comprise a storage device 108, such as a hard-drive, CD-ROM, or other storage medium for storing an operating system 116 and other programs, for example, a program 120 including computer executable instructions for, monitoring, evaluating, or acting on an evaluation of an operational characteristic of a particle sorting system as taught herein.

The computing device 102 may include a network interface 118 to interface to a Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 118 may comprise a built-in network adapter, network interface card, PCMCIA network card, card bus network adapter, wireless network adapter, USB network adapter, modem or any other device suitable for interfacing the computing device 102 to any type of network capable of communication and performing the operations described herein. Moreover, the computing device 102 may be any computer system such as a workstation, desktop computer, server, laptop, handheld computer or other form of computing or telecommunications device that is capable of communication and that has sufficient processor power and memory capacity to perform the operations described herein.

The computing device 102 can be running any operating system such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. The operating system may be running in native mode or emulated mode.

Figure 17:
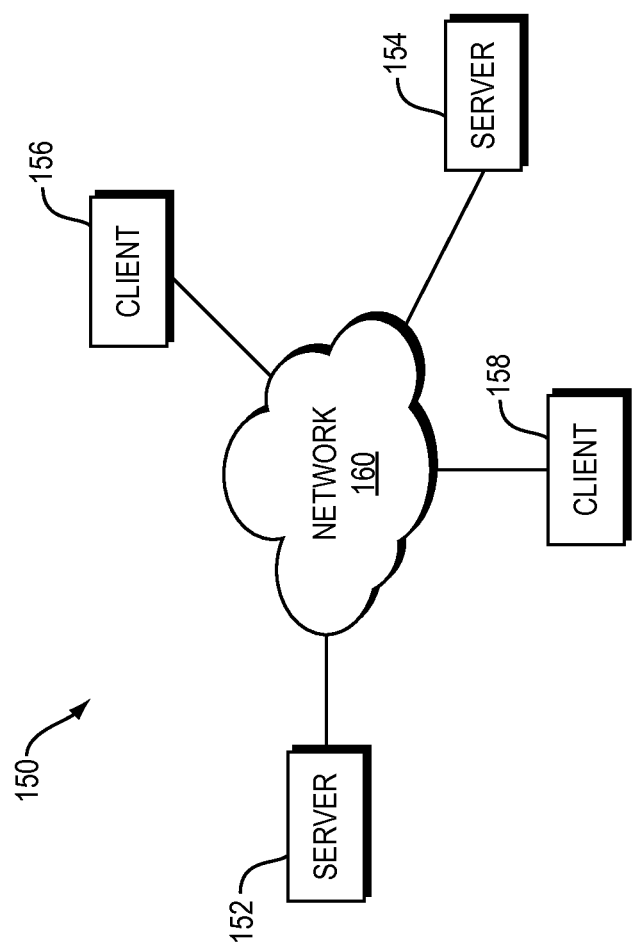
FIG. 17 depicts an exemplary network environment, according to the present disclosure.

FIG. 17 illustrates an exemplary network environment 150 suitable for a distributed implementation of exemplary embodiments. The network environment 150 may include one or more servers 152 and 154 coupled to clients 156 and 158 via a communication network 160. In one implementation, the servers 152 and 154 and/or the clients 156 and/or 158 may be implemented via the computing device 102. The network interface 118 of the computing device 102 enables the servers 152 and 154 to communicate with the clients 156 and 158 through the communication network 160. The communication network 160 may include Internet, intranet, LAN (Local Area Network), WAN (Wide Area Network), MAN (Metropolitan Area Network), wireless network (for example, using IEEE 802.11 or Bluetooth), or other network configurations. In addition the network may use middleware, such as CORBA (Common Object Request Broker Architecture) or DCOM (Distributed Component Object Model) to allow a computing device on the network 160 to communicate directly with another computing device that is connected to the network 160.

In the network environment 160, the servers 152 and 154 may provide the clients 156 and 158 with software components or products under a particular condition, such as a license agreement. The software components or products may include one or more components of the application 120. For example, the client 156 may evaluate an operational characteristic of a particle processing system over the server 152.

Figure 18:
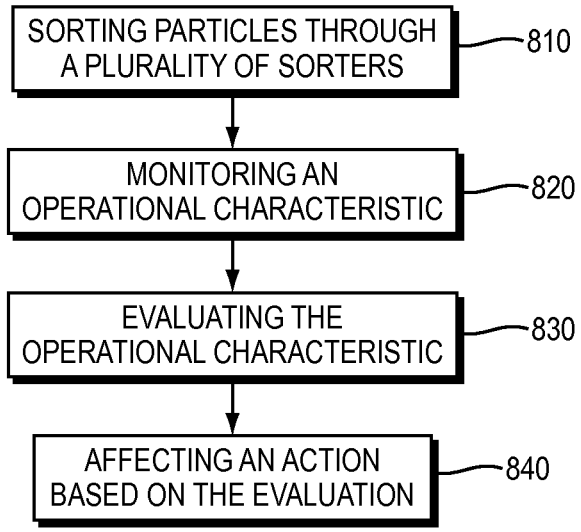
FIG. 18 depicts an exemplary method for processing particles, according to the present disclosure.

With reference now to FIG. 18, an exemplary method 800 for processing particles is depicted. The method 800 generally includes steps of sorting particles in a stream of particles suspended in a carrier fluid through a particle sorting system including a plurality of sorters (Step 810) and monitoring an operational characteristic of the particle sorting system (Step 820). In exemplary embodiments, the step of sorting particles (Step 810) may advantageously include characterizing the particles and sorting the particles based on the characterization thereof. In further exemplary embodiments, the exemplary method 800 may further include steps of evaluating, for example, using a processor, the operational characteristic (Step 830) and affecting an action, for example, a notification action or a corrective or proactive action based on such an evaluation (Step 840).

Figure 19:
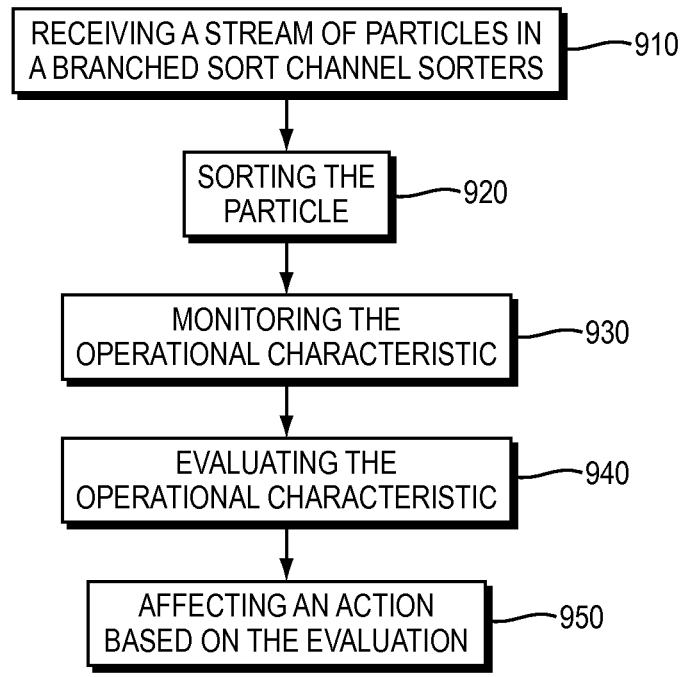
FIG. 19 depicts another exemplary method for processing particles, according to the present disclosure.

With reference now to FIG. 19, another exemplary method 900 for processing particles is depicted. The method 900 generally includes the steps of receiving a stream of particles suspended in a carrier liquid in a branched flow-channel of a sort module (Step 910); using a sorter to selectively sort the particles in the stream of suspended particles between a first output branch channel and a second output branch channel of the branched flow-channel (Step 920); and monitoring an operational characteristic of the sorter (Step 930). In exemplary embodiments, the step of sorting particles (Step 920) may advantageously include characterizing the particles and sorting the particles based on the characterization thereof. In further exemplary embodiments, the exemplary method 900 may further include steps of evaluating, for example, using a processor, the operational characteristic (Step 940) and affecting an action, for example, a notification action or a corrective or proactive action based on such an evaluation (Step 950).

Although the teachings herein have been described with reference to exemplary embodiments and implementations thereof, the disclosed methods, systems and media are not limited to such exemplary embodiments/implementations. Rather, as will be readily apparent to persons skilled in the art from the description taught herein, the disclosed methods, systems and media are susceptible to modifications, alterations and enhancements without departing from the spirit or scope hereof Accordingly, all such modifications, alterations and enhancements within the scope hereof are encompassed herein.

What is claimed:

1. A particle processing system comprising:
   a microfluidic sort module having a branched flow-channel defined in a substrate to receive a stream of particles, the branched flow-channel including a flow-path that branches at a branch point into a first output branch channel and a second output branch channel, the microfluidic sort module further having a particle sorter operable to selectively sort particles between the first output branch channel and the second output branch channel;
   a first sensor system optically coupled to the flow-path upstream of the branch point having focusing optics and a first optical sensor to sense a particle characteristic of a particle flowing through the flow path to control a sorting operation of the microfluidic sort module;

a capillary tube fluidically coupled to one of the first output branch channel or the second output branch channel; and a sort monitoring system having a second sensor system optically coupled to the capillary tube to monitor a performance of the sorting operation by detecting and collecting particle data that characterizes individual particles downstream of the particle sorter using focusing optics to direct light through the capillary tube and onto a second optical sensor to determine a statistically-based characteristic of a composition of a sorted sample from the data collected from the individual particles detected downstream of the particle sorter, and wherein the sort monitoring system is configured to real-time evaluate the statistically-based characteristic of the composition of the sorted sample.

2. The particle processing system of claim 1, further comprising a programmable controller responsive to an output of the sort monitoring system and configured to control one or more operations of the particle processing system.

3. The particle processing system of claim 1, further comprising a programmable controller configured to adjust a flow rate of the stream of suspended particles as the stream continues to flow through the particle sorter based on an evaluation of the statistically-based characteristic of the composition of the sorted sample.

4. The particle processing system of claim 1, wherein the sort monitoring system is configured to track a particle at different locations in the particle processing system.

5. The particle processing system of claim 1, further comprising a programmable controller configured to increase particle throughput when the evaluation of the statistically-based characteristic of the composition of the sorted sample relative to a predetermined sort performance criteria shows that the particle processing system is over performing.

6. The particle processing system of claim 1, wherein the sort monitoring system is configured to real-time evaluate the performance of the sorting operation based on one or more sort parameters, and wherein the one or more sort parameters include a baseline event rate or a baseline margin of error for one of the output branch channels.

7. The particle processing system of claim 1,
wherein the microfluidic sort module includes a plurality of the branched channels and a plurality of the particle sorters for sorting particles within the branched channels,
wherein the sort monitoring system includes a monitor sensor configured to monitor a statistically-based operational characteristic of a sorted sample, and
wherein the sort monitoring system is configured to real-time evaluate a collective performance of the plurality of particle sorters.

8. The particle processing system of claim 7, wherein the monitor sensor is configured to detect a presence or an absence of particles in a first monitor region downstream of at least two of the sorters.

9. The particle processing system of claim 7, wherein the monitor sensor is configured to monitor a merged output of at least two of the sorters.

10. The particle processing system of claim 7, wherein the monitor sensor is configured to monitor an individual output of one of the sorters.

11. The particle processing system of claim 10, wherein the monitoring system further includes a second monitor sensor configured to monitor a merged output of at least two of the sorters.

12. The particle processing system of claim 7, wherein a first of the sorters is upstream of a second of the sorters and the monitor sensor is configured to detect a presence or absence of particles at monitor region downstream of both the first and second of the sorters.

13. The particle processing system of claim 7, wherein the monitor sensor is configured to detect a presence or absence particles at a monitor region downstream of a first of the sorters and upstream of a second of the sorters.

14. The particle processing system of claim 13, wherein the monitoring system further comprises a second monitor sensor configured to detect a presence or absence of particles at a second monitor region downstream of the second of the sorters.

15. The particle processing system of claim 7, wherein the operational characteristic is related to a collective performance of a plurality of the sorters.

16. The particle processing system of claim 7, wherein the operational characteristic is related to an individual performance of one of the sorters.

17. The particle processing system of claim 7, further comprising a programmable microprocessor for evaluating the operational characteristic and taking an action based thereon.

18. A method for processing particles flowing through a particle sorting system, the method comprising:
receiving a stream of particles in a branched flow-channel defined in a substrate of the particle sorting system, the branched flow-channel including a flow-path that branches at a branch point into a first output branch channel and a second output branch channel;
detecting a particle characteristic of one or more of the particles in the stream of particles using a first sensor system optically coupled to the flow-path having focusing optics and a first optical sensor;
using a particle sorter to selectively sort the particles in the stream of suspended particles between the first output branch channel and the second output branch channel based on the detected particle characteristic;
flowing particles from one of the first output branch channel or the second output branch through a capillary tube fluidically coupled to the substrate;
monitoring a sorting operation of the particle sorter using a second sensor system having focusing optics to direct light through the capillary tube and onto a second optical sensor to detect and collect particle data that characterizes individual particles downstream of the particle sorter to determine a statistically-based characteristic of a composition of a sorted sample from the data collected from the individual particles detected downstream of the particle sorter; and
evaluating the statistically-based characteristic of the composition of the sorted sample in real-time relative to a predetermined sort performance criteria.

19. The method of claim 18, further comprising controlling the operation of the particle sorting system based on the evaluated statistically-based characteristic of the composition of the sorted sample.

20. The method of claim 18, further comprising adjusting a flow rate of the stream of suspended particles as the stream continues to flow through the particle sorting system based on an evaluation of the statistically-based characteristic of the composition of the sorted sample.

21. The method of claim 18, further comprising tracking a particle at different locations in the particle sorting system.

22. The method of claim 18, further comprising increasing particle throughput when the evaluation of the statistically-based characteristic of the composition of the sorted sample relative to the predetermined sort performance criteria shows that the particle sorting system is over performing.

23. The particle processing system of claim 18, wherein the predetermined sort performance criteria include a baseline event rate or a baseline margin of error for one of the output branch channels.

24. The method of claim 18, wherein the particle sorting system includes a plurality of particle sorters, the method further comprising:
   sorting particles in the plurality of particle sorters; and
   evaluating in real-time a collective performance of the plurality of particle sorters.

25. The method of claim 24, further comprising detecting a presence or an absence of particles in a first monitor region downstream of at least two of the particle sorters.

26. The method of claim 24, further comprising monitoring a merged output of at least two of the particle sorters.

27. The method of claim 24, further comprising monitoring an individual output of one of the particle sorters.

28. The method of claim 24, further comprising detecting a presence or absence of particles at monitor region downstream of both a first and second of the particle sorters, wherein the first of the particle sorters is upstream of the second of the particle sorters.

29. The method of claim 24, further comprising detecting a presence or absence particles at a monitor region downstream of a first of the particle sorters and upstream of a second of the particle sorters.

30. The method of claim 29, further comprising detecting a presence or absence of particles at a second monitor region downstream of the second of the particle sorters.

31. The method of claim 24, wherein the statistically-based operational characteristic is related to a collective performance of a plurality of the particle sorters.

32. The method of claim 24, wherein the statistically-based operational characteristic is related to an individual performance of one of the particle sorters.

33. The method of claim 24, further comprising evaluating the statistically-based operational characteristic and taking an action based thereon.

34. The particle processing system of claim 1, wherein the sort monitoring system is a modular component of the particle processing system separate from the particle sorter.

35. The particle processing system of claim 34, wherein the sort monitoring system is an interchangeable component of the particle processing system.

36. The particle processing system of claim 34, wherein the sort monitoring system includes a cutout for receiving a flow-channel associated with an output of the particle sorter.

37. The method of claim 18, further comprising:
   monitoring an electric property for a pair of conductive tracers associated with a channel; and
   detecting a particle in the channel based on changes in the monitored electric property.

38. The method of claim 37, wherein the channel is an output branch channel of a sorter module for sorting particles.

39. The method of claim 37, wherein the electric property is a conductive property of the tracers across the channel.

40. The method of claim 37, wherein the electric property is a capacitive property of the tracers across the channel.

41. The particle processing system of claim 1, further comprising:
   a pair of conductive tracers associated with a channel; and
   a detector system adapted to monitor an electric property across the pair of conductive tracers and detect a particle in the channel based on changes in the monitored electric property.

42. The particle processing system of claim 1, wherein the statistically-based operational characteristic of the sorted sample is at least one of a purity of the sorted sample, a retention of a predetermined particle type in the sorted sample, an exclusion of a predetermined particle type in the sorted sample, an expected sort particle count of the sorted sample, a sort fraction of the sorted sample, or a sort accuracy of the sorted sample.

\* \* \* \* \*